(12) United States Patent
Degen et al.

(10) Patent No.: US 7,750,194 B2
(45) Date of Patent: Jul. 6, 2010

(54) PROCESS FOR PREPARING ISOPROPANOL AND 2-BUTANOL FROM THE CORRESPONDING ALKANES

(75) Inventors: Georg Degen, Lorsch (DE); Sven Crone, Limburgerhof (DE); Ralf Boehling, Lorsch (DE); Ansgar Gereon Altenhoff, Heidelberg (DE); Wolfgang Rohde, Speyer (DE); Jochen Buerkle, Mannheim (DE); Goetz-Peter Schindler, Ludwigshafen (DE); Thomas Holtmann, Speyer (DE); Markus Schmitt, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/374,351

(22) PCT Filed: Jul. 16, 2007

(86) PCT No.: PCT/EP2007/057289

§ 371 (c)(1),
(2), (4) Date: Nov. 2, 2009

(87) PCT Pub. No.: WO2008/009648

PCT Pub. Date: Jan. 24, 2008

(65) Prior Publication Data

US 2010/0048960 A1 Feb. 25, 2010

(30) Foreign Application Priority Data

Jul. 20, 2006 (EP) .................................. 06117568

(51) Int. Cl.
C07C 29/09 (2006.01)

(52) U.S. Cl. ...................................... 568/889; 568/886

(58) Field of Classification Search ................. 568/886, 568/889

See application file for complete search history.

(56) References Cited

U.S. PATENT DOCUMENTS

| | | | |
|---|---|---|---|
| 4,384,148 A | 5/1983 | Schmidt | |
| 4,484,013 A | 11/1984 | Schmidt | |
| 4,788,371 A | 11/1988 | Imai et al. | |
| 5,220,091 A | 6/1993 | Brinkmeyer et al. | |
| 5,430,220 A | 7/1995 | Khare et al. | |
| 5,877,369 A | 3/1999 | Wu et al. | |
| 6,414,209 B1 | 7/2002 | Herskowitz et al. | |
| 6,670,303 B1 | 12/2003 | Heineke et al. | |
| 6,781,017 B2 | 8/2004 | Machhammer et al. | |
| 7,291,761 B2 | 11/2007 | Machhammer et al. | |

2004/0225165 A1  11/2004  Allison et al.

FOREIGN PATENT DOCUMENTS

| | | |
|---|---|---|
| DE | 3003126 A1 | 7/1980 |
| DE | 19937105 A1 | 2/2001 |
| DE | 19937106 A1 | 2/2001 |
| DE | 19937107 A1 | 2/2001 |
| DE | 10028582 A1 | 12/2001 |
| DE | 10211275 A1 | 9/2003 |
| DE | 10245585 A1 | 4/2004 |
| DE | 10246119 A1 | 4/2004 |
| EP | 0117146 A1 | 8/1984 |
| EP | 0705136 B1 | 4/1996 |
| GB | 2041364 A | 9/1980 |
| GB | 2147290 A | 5/1985 |
| GB | 2238539 A | 6/1991 |
| WO | WO 99/29420 A1 | 6/1999 |
| WO | WO 99/46039 A1 | 9/1999 |

*Primary Examiner*—Elvis O Price
(74) *Attorney, Agent, or Firm*—Connolly Bove Lodge & Hutz LLP

(57) ABSTRACT

A process for preparing alkanols (I) selected from the group consisting of isopropanol and 2-butanol from the corresponding alkanes (II) selected from the group consisting of propane and n-butane, comprising the steps of:

A) providing a starting gas stream a comprising the alkane (II);
B) feeding the starting gas stream a comprising the alkane (II) into a dehydrogenation zone and subjecting the alkane (II) to a dehydrogenation to the alkene (III) to obtain a product gas stream b comprising the alkene (III) and unconverted alkane (II), with or without high boilers, steam, hydrogen and low boilers;
C) at least compressing product gas stream b, optionally separating product gas stream b into an aqueous phase c1, a phase c2 comprising the alkene (III) and the alkane (II), with or without high boilers, and a gas phase c3 comprising hydrogen and low boilers;
D) reacting product gas stream b or the phase c2 comprising alkene (III) and alkane (II) with an organic acid (IV) in an esterification zone to obtain a product mixture d comprising the corresponding alkyl ester (V) of the organic acid and the unconverted alkane (II);
E) removing from product mixture d a gas stream e1 which comprises an alkane (II) and is recycled into the dehydrogenation zone if appropriate, and a product mixture e2 comprising the alkyl ester;
F) reacting the product mixture e2 comprising the alkyl ester with water in an ester hydrolysis zone to give a product mixture f comprising the alkanol (I) and the organic acid (IV);
G) removing the alkanol (I) and the organic acid (IV) from product mixture f and, if appropriate, recycling the organic acid into the esterification zone.

21 Claims, 4 Drawing Sheets

PROCESS FOR PREPARING ISOPROPANOL AND 2-BUTANOL FROM THE CORRESPONDING ALKANES

RELATED APPLICATIONS

This application is a national stage application (under 35 U.S.C. §371) of PCT/EP2007/057289, filed Jul. 16, 2007, which claims benefit of European Application No. 06117568.3, filed Jul. 20, 2006.

The invention relates to a process for preparing isopropanol from propane and 2-butanol from butane.

The hydration of alkenes to alcohols is well known and is performed on the industrial scale. In industry, two-stage hydration is practiced, in which the alkene is reacted with sulfuric acid to give the alkyl sulfate and this is hydrolyzed in the second step with water to give the alcohol and the acid. It is advantageous in this process that the alkene can be used in the form of crude alkene mixtures, for example mixtures of the alkene, the corresponding alkane and further secondary constituents. Disadvantages are the highly corrosive medium, the contamination of the product with sulfur-containing odor-forming substances which can necessitate additional purification steps, and the loss of the inert alkane fraction of the mixture, which does not react and is discharged after the reaction. A further disadvantage is that, after hydrolysis of the alkyl sulfate to the alcohol, the resulting dilute sulfuric acid has to be concentrated before it is reused in the esterification step.

In addition, the esterification of olefins with carboxylic acids and subsequent ester hydrolysis of the alkyl esters formed to the corresponding alcohol with recovery of the acid is known. For instance, U.S. Pat. No. 4,384,148 describes the reaction of ethene with acetic acid to give ethyl acetate in an autoclave. The subsequent hydrolysis of the ethyl acetate removed by distillation with water in a molar ratio of 1:5 in an autoclave affords a mixture comprising ethyl acetate, ethanol and diethyl ether. GB 2 238 539 discloses the two-stage hydration of 1-butene by reaction with trifluoroacetic acid to give 2-butyl trifluoroacetate in the presence of a highly acidic ion exchange resin and subsequent hydrolysis of the ester to give 2-butanol.

In addition, direct one-stage hydration of alkenes over strongly acidic catalysts, for example ion exchangers, zeolites, heteropolyacids and mineral acids, on heterogeneous supports is performed industrially. Processes for direct hydration can be performed in the gas phase, in the liquid phase or by biphasic means. Disadvantages of the one-stage processes are in particular the low conversions and the high requirements on the purity of the alkene used. For example, propylene has to be used in the form of polymer-grade propylene.

GB-A 2 147 290 describes a process for preparing isopropanol, 2-butanol and methyl tert-butyl ether from an LPG mixture comprising propane, n-butane and isobutane. The gas mixture is dehydrogenated to a mixture comprising propene, n-butenes and isobutene and subsequently passes through an etherification zone in which isobutene is etherified with methanol to give methyl tert-butyl ether. Propene and n-butenes, which essentially do not react with methanol under the conditions selected, are simultaneously hydrated directly with water to give isopropanol and 2-butanol respectively.

US 2004/0225165 A discloses a process for preparing alcohols having 3 or more carbon atoms from the corresponding alkanes, in which a stream comprising propane or a longer-chain alkane is converted to an intermediate stream comprising the corresponding olefin, and the intermediate stream is converted by direct or indirect hydration to a product stream comprising the corresponding alcohol The document mentions, as an indirect process, the two-stage hydration of propene with concentrated sulfuric acid with intermediate formation of the sulfuric ester and subsequent hydrolysis of the sulfuric ester to the alcohol. In addition, various processes for direct hydration are described.

U.S. Pat. No. 4,484,013 discloses a process for preparing isopropanol and tort-butanol in which a starting gas stream composed of propane and isobutane is fed into a dehydrogenation zone and dehydrogenated to give a product gas mixture comprising propene, isobutene and unconverted propane and isobutane by nonoxidative means, i.e. in the absence of air or oxygen. First low boilers (hydrogen) and then propane are removed by distillation from the product gas stream of the dehydrogenation, the latter being recycled into the dehydrogenation zone. The remaining gas stream which consists essentially of propene, isobutene and isobutane is fed into a hydration zone, where propene and isobutene are hydrated over an acidic ion exchange resin directly to isopropanol and tert-butanol. The remaining gas stream is separated firstly into an isobutane stream which is recycled into the dehydrogenation zone and secondly into a stream comprising propane and propene, which is recycled into the propane removal before the hydration step. The process is thus characterized in that unconverted propane is removed before the hydration and the hydration is performed with a starting stream consisting essentially of the $C_3$- and $C_4$-olefins.

It is an object of the invention to provide an economically viable process for preparing isopropanol and 2-butanol, which does not have the disadvantages of the prior art.

The object is achieved by a process for preparing alkanols (I) selected from the group consisting of isopropanol and 2-butanol from the corresponding alkanes (II) selected from the group consisting of propane and n-butane, comprising the steps of:

A) providing a starting gas stream a comprising the alkane (II);

B) feeding the starting gas stream a comprising the alkane (II) into a dehydrogenation zone and subjecting the alkane (II) to a dehydrogenation to the alkene (III) to obtain a product gas stream b comprising the alkene (III) and unconverted alkane (II), with or without high boilers, steam, hydrogen and low boilers;

C) at least compressing product gas stream b, optionally separating product gas stream b into an aqueous phase c1, a phase c2 comprising the alkene (III) and the alkane (II), with or without high boilers, and a gas phase c3 comprising hydrogen and low boilers;

D) reacting product gas stream b or the phase c2 comprising alkene (III) and alkane (II) with an organic acid (IV) in an esterification zone to obtain a product mixture d comprising the corresponding alkyl ester (V) of the organic acid and the unconverted alkane (II);

E) removing from product mixture d a gas stream e1 which comprises an alkane (II) and is recycled into the dehydrogenation zone if appropriate, and a product mixture e2 comprising the alkyl ester;

F) reacting the product mixture e2 comprising the alkyl ester with water in an ester hydrolysis zone to give a product mixture f comprising the alkanol (I) and the organic acid (IV);

G) removing the alkanol (I) and the organic acid (IV) from product mixture f and, if appropriate, recycling the organic acid into the esterification zone.

Figure 1:
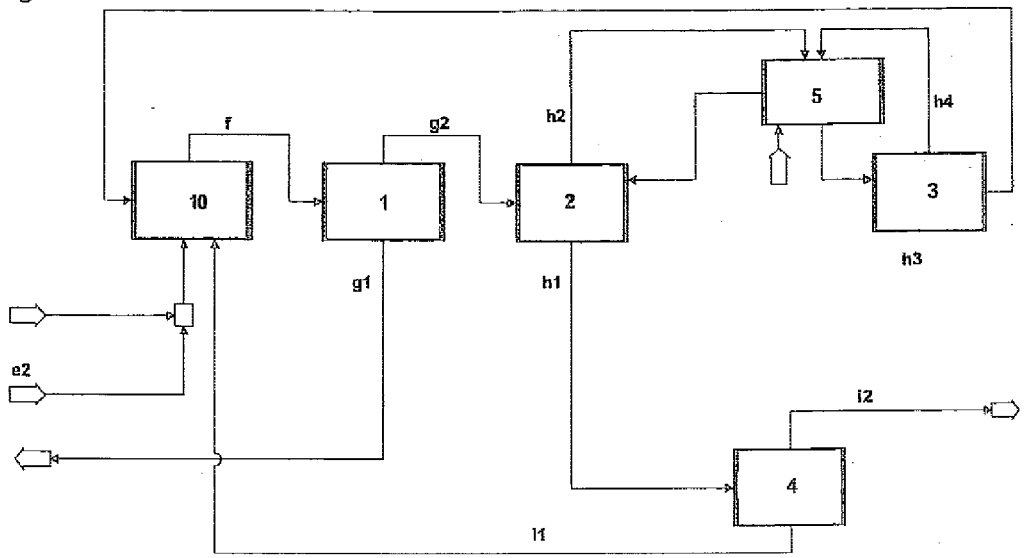
FIGS. 1-8 are schematic representations of process variants of the present invention.

The process according to the invention dispenses with the use of highly corrosive sulfuric acid. It is notable in that, nevertheless, high space-time yields and conversions are achieved in the esterification step D) even when a starting gas stream is used which comprises the alkene (I) only in very dilute form in addition to further components (unconverted alkane, inert gases). A removal of unreactive secondary components before the esterification step is performed can therefore be dispensed with. Since the ester hydrolysis step F) can be performed with water in stoichiometric deficiency, it is also possible to obtain the organic acid (IV) in concentrated form and to recycle it directly, without further concentration, into the esterification step D).

In the first process part A), a starting gas stream a comprising alkane (II) selected from propane and butane is provided. In the case of propane, this stream comprises generally at least 80% by volume of propane, preferably 90% by volume of propane. In addition, it generally also comprises butanes (n-butane, isobutane), butenes, ethane and ethene. Typical compositions of the propane-containing starting gas stream are disclosed in DE-A 102 46 119 and DE-A 102 45 585. Typically, the propane-containing starting gas stream a is obtained from liquefied petroleum gas (LPG).

In the case of n-butane as the alkane (II), the starting gas stream comprises generally at least 80% by volume of n-butane, preferably 90% by volume of n-butane. In addition, it generally also comprises ethane, ethene, propane, propene, isobutane, butenes and $C_5$ hydrocarbons.

In one process part B), the starting gas stream comprising the alkane (II) is fed into a dehydrogenation zone and subjected to a generally catalytic dehydrogenation. In this step, the alkane is dehydrogenated partly to the alkene over a dehydrogenation-active catalyst in a dehydrogenation reactor. In addition, hydrogen and small amounts of low boilers and high boilers are obtained. In the present context, low boilers refer to hydrocarbons having lower boiling points than propene or 1-butene; high boilers refer to hydrocarbons having higher boiling points than propane or 2-butene. For example, the low boilers obtained in the propane dehydrogenation may be methane, ethane and ethene, and the high boilers $C_4^+$ hydrocarbons (n-butane, isobutane, butenes, butadiene). In the n-butane dehydrogenation, the low boilers obtained may, for example, be methane, ethane and ethene, propane and propene, and the high boilers $C_5^+$ hydrocarbons. In addition, if the dehydrogenation is performed in the presence of an oxygenous gas, generally carbon oxides (CO, $CO_2$), especially $CO_2$, and steam, with or without a small amount of inert gases, are obtained in the product gas mixture of the dehydrogenation. The product gas stream of the dehydrogenation generally comprises steam which has already been added to the dehydrogenation gas mixture and/or—in the case of dehydrogenation in the presence of oxygen (oxidative or nonoxidative)—is formed in the dehydrogenation. When the dehydrogenation is performed in the presence of oxygen, inert gases (nitrogen) are introduced into the dehydrogenation zone with the oxygenous gas stream fed in, unless pure oxygen is fed in. In addition, unconverted alkane (II) (propane and/or n-butane) is present in the reaction gas mixture.

The alkane dehydrogenation can in principle be performed in all reactor types known from the prior art. A comparatively comprehensive description of reactor types suitable in accordance with the invention is also present in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

The dehydrogenation can be performed as an oxidative or nonoxidative hydrogenation. The dehydrogenation can be performed isothermally or adiabatically. The dehydrogenation can be performed catalytically in a fixed bed reactor, moving bed reactor or fluidized bed reactor.

The nonoxidative catalytic alkane dehydrogenation is preferably performed autothermally. To this end, oxygen is additionally admixed to the reaction gas mixture of the dehydrogenation in at least one reaction zone, and the hydrogen and/or hydrocarbon present in the reaction gas mixture is combusted at least partly, which generates at least some of the heat of dehydrogenation required in the at least one reaction zone directly in the reaction gas mixture.

One feature of the nonoxidative method compared to an oxidative method is the at least intermediate formation of hydrogen, which is manifested in the presence of hydrogen in the product gas of the dehydrogenation. In the oxidative dehydrogenation, no free hydrogen is found in the product gas of the dehydrogenation.

A suitable reactor form is the fixed bed tubular or tube bundle reactor. In these reactors, the catalyst (dehydrogenation catalyst and if appropriate a specialized oxidation catalyst) is disposed as a fixed bed in a reaction tube or in a bundle of reaction tubes. Customary reaction tube internal diameters are from about 10 to 15 cm. A typical dehydrogenation tube bundle reactor comprises from about 300 to 1000 reaction tubes. The internal temperature in the reaction tubes typically varies in the range from 300 to 1200° C., preferably in the range from 500 to 1000° C. The working pressure is customarily from 0.5 to 8 bar, frequently from 1 to 2 bar, when a low steam dilution is used, or else from 3 to 8 bar when a high steam dilution is used (corresponding to the steam active reforming process (STAR process) or the Linde process) for the dehydrogenation of propane or butane of Phillips Petroleum Co. Typical gas hourly space velocities (GHSV) are from 500 to 2000 $h^{-1}$, based on hydrocarbon used. The catalyst geometry may, for example, be spherical or cylindrical (hollow or solid). It is also possible to operate a plurality of fixed bed tubular reactors or tube bundle reactors alongside one another, of which at least one is alternately in the state of regeneration.

The nonoxidative catalytic, autothermal dehydrogenation may also be carried out under heterogeneous catalysis in a fluidized bed, according to the Snamprogetti/Yarsintez-FBD process. Appropriately, two fluidized beds are operated in parallel, of which one is generally in the state of regeneration. The working pressure is typically from 1 to 2 bar, the dehydrogenation temperature generally from 550 to 600° C. The heat required for the dehydrogenation can be introduced into the reaction system by preheating the dehydrogenation catalyst to the reaction temperature. The admixing of a cofeed comprising oxygen allows the preheater to be dispensed with and the required heat to be generated directly in the reactor system by combustion of hydrogen and/or hydrocarbons in the presence of oxygen. If appropriate, a cofeed comprising hydrogen may additionally be admixed.

The nonoxidative catalytic, autothermal dehydrogenation is preferably carried out in a tray reactor. This reactor comprises one or more successive catalyst beds. The number of catalyst beds may be from 1 to 20, advantageously from 1 to 6, preferably from 1 to 4 and in particular from 1 to 3. The catalyst beds are preferably flowed through radially or axially by the reaction gas. In general, such a tray reactor is operated using a fixed catalyst bed. In the simplest case, the fixed catalyst beds are disposed axially in a shaft furnace reactor or in the annular gaps of concentric cylindrical grids. A shaft furnace reactor corresponds to one tray. The performance of the dehydrogenation in a single shaft furnace reactor corresponds to one embodiment. In a further, preferred embodiment, the dehydrogenation is carried out in a tray reactor having 3 catalyst beds.

In general, the amount of the oxygenous gas added to the reaction gas mixture is selected in such a way that the amount of heat required for the dehydrogenation of the alkane (propane and/or n-butane) is generated by the combustion of the hydrogen present in the reaction gas mixture and of any hydrocarbons present in the reaction gas mixture and/or of carbon present in the form of coke. In general, the total amount of oxygen supplied, based on the total amount of propane, is from 0.001 to 0.5 mol/mol, preferably from 0.005 to 0.25 mol/mol, more preferably from 0.05 to 0.25 mol/mol. Oxygen may be used either in the form of pure oxygen or in the form of oxygenous gas which comprises inert gases. In order to prevent high propane and propene losses in the workup (see below), it may be advantageous when the oxygen content of the oxygenous gas used is high and is at least 50% by volume, preferably at least 80% by volume, more preferably at least 90% by volume. A particularly preferred oxygenous gas is oxygen of technical-grade purity with an $O_2$ content of approx. 99% by volume. In addition, a method is possible in which air is fed in as the oxygenous gas.

The hydrogen combusted to generate heat is the hydrogen formed in the catalytic alkane dehydrogenation and also any hydrogen additionally added to the reaction gas mixture as hydrogenous gas. The amount of hydrogen present should preferably be such that the molar $H_2/O_2$ ratio in the reaction gas mixture immediately after the oxygen is fed in is from 1 to 10 mol/mol, preferably from 2 to 5 mol/mol. In multistage reactors, this applies to every intermediate feed of oxygenous and any hydrogenous gas.

The hydrogen is combusted catalytically. The dehydrogenation catalyst used generally also catalyzes the combustion of the hydrocarbons and of hydrogen with oxygen, so that in principle no specialized oxidation catalyst is required apart from it. In one embodiment, operation is effected in the presence of one or more oxidation catalysts which selectively catalyze the combustion of hydrogen to oxygen in the presence of hydrocarbons. The combustion of these hydrocarbons with oxygen to give CO, $CO_2$ and water therefore proceeds only to a minor extent. The dehydrogenation catalyst and the oxidation catalyst are preferably present in different reaction zones.

When the reaction is carried out in more than one stage, the oxidation catalyst may be present only in one, in more than one or in all reaction zones.

Preference is given to disposing the catalyst which selectively catalyzes the oxidation of hydrogen at the points where there are higher partial oxygen pressures than at other points in the reactor, in particular near the feed point for the oxygenous gas. The oxygenous gas and/or hydrogenous gas may be fed in at one or more points in the reactor.

In one embodiment of the process according to the invention, there is intermediate feeding of oxygenous gas and of hydrogenous gas upstream of each tray of a tray reactor. In a further embodiment of the process according to the invention, oxygenous gas and hydrogenous gas are fed in upstream of each tray except the first tray. In one embodiment, a layer of a specialized oxidation catalyst is present downstream of every feed point, followed by a layer of the dehydrogenation catalyst. In a further embodiment, no specialized oxidation catalyst is present. The dehydrogenation temperature is generally from 400 to 1100° C.; the pressure in the last catalyst bed of the tray reactor is generally from 0.2 to 5 bar, preferably from 1 to 3 bar. The GHSV (gas hourly space velocity) is generally from 500 to 2000 $h^{-1}$, and, in high-load operation, even up to 100 000 $h^{-1}$, preferably from 4000 to 16 000 $h^{-1}$.

A preferred catalyst which selectively catalyzes the combustion of hydrogen comprises oxides and/or phosphates selected from the group consisting of the oxides and/or phosphates of germanium, tin, lead, arsenic, antimony and bismuth. A further preferred catalyst which catalyzes the combustion of hydrogen comprises a noble metal of transition group VIII and/or I of the periodic table.

The dehydrogenation catalysts used generally have a support and an active composition. The support generally consists of a heat-resistant oxide or mixed oxide. The dehydrogenation catalysts preferably comprise a metal oxide which is selected from the group consisting of zirconium dioxide, zinc oxide, aluminum oxide, silicon dioxide, titanium dioxide, magnesium oxide, lanthanum oxide, cerium oxide and mixtures thereof, as a support. The mixtures may be physical mixtures or else chemical mixed phases such as magnesium aluminum oxide or zinc aluminum oxide mixed oxides. Preferred supports are zirconium dioxide and/or silicon dioxide; particular preference is given to mixtures of zirconium dioxide and silicon dioxide.

The active composition of the dehydrogenation catalysts generally comprises one or more elements of transition group VIII, preferably platinum and/or palladium, more preferably platinum. Furthermore, the dehydrogenation catalysts may comprise one or more elements of main group I and/or II, preferably potassium and/or cesium. The dehydrogenation catalysts may further comprise one or more elements of transition group III including the lanthanides and actinides, preferably lanthanum and/or cerium. Finally, the dehydrogenation catalysts may comprise one or more elements of main group III and/or IV, preferably one or more elements from the group consisting of boron, gallium, silicon, germanium, tin and lead, more preferably tin.

In a preferred embodiment, the dehydrogenation catalyst comprises at least one element of transition group VIII, at least one element of main group I and/or II, at least one element of main group III and/or IV and at least one element of transition group III including the lanthanides and actinides.

For example, all dehydrogenation catalysts which are disclosed by WO 99/46039, U.S. Pat. No. 4,788,371, EP-A 705 136, WO 99/29420, U.S. Pat. Nos. 5,220,091, 5,430,220, 5,877,369, EP 0 117 146, DE-A 199 37 106, DE-A 199 37 105 and DE-A 199 37 107 may be used in accordance with the invention. Particularly preferred catalysts for the above-described variants of autothermal propane dehydrogenation are the catalysts according to examples 1, 2, 3 and 4 of DE-A 199 37 107.

Preference is given to carrying out the autothermal alkane dehydrogenation in the presence of steam. The added steam serves as a heat carrier and supports the gasification of organic deposits on the catalysts, which counteracts carbonization of the catalysts and increases the lifetime of the catalysts. This converts the organic deposits to carbon monoxide, carbon dioxide and in some cases water.

The dehydrogenation catalyst may be regenerated in a manner known per se. For instance, steam may be added to the reaction gas mixture or a gas comprising oxygen may be passed from time to time over the catalyst bed at elevated temperature and the deposited carbon burnt off. The dilution with steam shifts the equilibrium toward the products of dehydrogenation. After the regeneration, the catalyst is reduced with a hydrogenous gas if appropriate.

In the autothermal propane dehydrogenation with feeding of essentially pure oxygen, a gas mixture is obtained which generally has the following composition: from 10 to 45% by volume of propane, from 5 to 40% by volume of propene, from 0 to 5% by volume of methane, ethane, ethene and $C_4^+$ hydrocarbons, from 0 to 5% by volume of carbon dioxide, from 0 to 20% by volume of steam and from 0 to 25% by volume of hydrogen, and also from 0 to 5% by volume of inert gases.

In the autothermal butane dehydrogenation with feeding of essentially pure oxygen, a gas mixture is obtained which generally has the following composition: from 5 to 40% by volume of butane, from 10 to 60% by volume of 1-butene and 2-butene, from 0 to 10% by volume of methane, ethane, ethene, propane, propene and $C_5^+$ hydrocarbons, from 0 to 5% by volume of carbon dioxide, from 0 to 20% by volume of steam and from 0 to 25% by volume of hydrogen, and also from 0 to 5% by volume of inert gases.

When it leaves the dehydrogenation zone, product gas stream b is generally under a pressure of from 1 to 5 bar, preferably from 1.5 to 3 bar, and has a temperature in the range from 400 to 700° C.

Product gas stream b may be separated into two substreams, in which case one substream is recycled into the autothermal dehydrogenation, corresponding to the cycle gas method described in DE-A 102 11 275 and DE-A 100 28 582.

In process part C), product gas stream b is compressed. The compression of product gas stream b is effected to pressures of 5-150 bar, preferably to 15-100 bar, more preferably to 20-60 bar. The compression can be effected in a plurality of stages with intermediate cooling stages, for example in three or four stages; it is preferably effected in a plurality of stages, for example three stages. In one embodiment of the process according to the invention, product gas stream b is compressed in one or two stages to a pressure in the range from 5 to 12 bar and then in one or two stages to a pressure in the range from 10 to 25 bar. The cooling can also be effected in a plurality of stages and is preferably effected in a plurality of stages. The coolants used include air in air coolers, river water or cold water, and coolants such as ethene, propene and propane, which are cooled to temperatures in the range from −40° C. to −100° C. by compressing to pressures up to 20 bar and then decompressing.

Optionally, product gas stream b is separated into an aqueous phase c1, a hydrocarbon phase c2 comprising the alkene (III) and the unconverted alkane (II), and a gas phase c3 comprising hydrogen and low boilers.

The removal step within process step C) is effected generally when product gas stream b comprises steam. However, it is also possible to effect only a water removal (see below).

It is possible first to remove water from product gas stream b. The removal of water can be effected by condensing, by cooling and if appropriate compressing product gas stream b, and can be performed in one or more cooling stages and if appropriate compression stages. In general, product gas stream b is cooled for this purpose to a temperature in the range from 30 to 80° C., preferably from 40 to 65° C. The condensation can be effected before the compression and/or in the compression stages as an intermediate cooling.

In one embodiment of the process according to the invention, product gas stream b is conducted through a battery of heat exchangers and thus cooled first to a temperature in the range from 50 to 200° C. and then further to a temperature of from 40 to 80° C., for example 55° C., in a quench tower with water. This condenses out the majority of the steam, but also some of the high boilers present in product gas stream b. In the case of propane dehydrogenation, these may be $C_4^+$ hydrocarbons, especially the $C_5^+$ hydrocarbons.

This affords a steam-depleted product gas stream b. It generally still comprises up to 5% by volume of steam. For virtually full removal of water from product gas stream b, a drying step by means of molecular sieve can be provided.

When the autothermal alkane dehydrogenation is performed with feeding of pure oxygen or with oxygen-enriched air as the oxygenous gas, product gas stream b can be worked up and the alkane- and alkene-comprising mixtures c2 can be obtained also as described below.

Subsequently, product gas stream b is cooled and a liquid hydrocarbon stream c2 comprising propane and propene and/or n-butane and butenes is removed by condensation to leave a residual gas stream c3 comprising hydrogen and low boilers. In the case of propane dehydrogenation, the hydrocarbon stream c2 may additionally comprise methane, ethane, ethene and $C_4^+$ hydrocarbons; it generally comprises at least small amounts of ethane and ethene. The temperature and the pressure in the removal step within compression stage C can also be selected such that a majority of the alkanes and alkenes present in product gas stream b are present in gas stream c3. Just like the hydrocarbon stream c2, this gas stream c3 can be conducted into the esterification zone D or, alternatively, into an absorption stage (as described below).

In the case of n-butane dehydrogenation, the conditions are selected such that quite overwhelmingly n-butane and butenes condense out. The residual gas stream c3 comprises, in addition to hydrogen, generally also methane and carbon monoxide as low boilers. In addition, it may also comprise ethane and ethene and—if the autothermal dehydrogenation is not performed with feeding of pure oxygen—especially nitrogen and noble gases (mainly argon). It may additionally also comprise $C_3$- and $C_4$-hydrocarbons. To this end, product gas stream b is compressed generally to a pressure in the range from 5 to 60 bar and cooled to a temperature in the range from −10 to −60° C.

As well as the hydrocarbon stream c2, cooling and compression can also condense out an aqueous phase c1 which can be removed from the $C_3$ hydrocarbon phase c2 by phase separation in a phase separator if complete water removal from product gas stream b has not been effected before the condensation step. In the case of multistage cooling and compression, all condensate streams obtained can be fed to the phase separator.

It is also possible to dispense with preceding removal of water from product gas stream b before the condensation of the $C_3$ hydrocarbon phase c2. In that case, water condenses out as an aqueous phase c1 together with the alkane- and alkene-comprising hydrocarbon phase c2. Aqueous phase and hydrocarbon phase are then subsequently separated in a phase separator.

In general, the product gas stream is cooled by heat exchange with a coolant. The cooling can be effected in several stages using a plurality of cooling circuits. The cooling can be effected in several stages in a column, in which case the gas ascending within the column is withdrawn, cooled, (partly) condensed and recycled into the column. The condensate is withdrawn at the bottom of the column, and the uncondensed gas which has not condensed in the uppermost cooling circuit either at the top of the column.

When the alkane dehydrogenation is performed as an autothermal dehydrogenation with simultaneous combustion of the hydrogen formed, the result is a low hydrogen content of product gas stream b. As a consequence, it is possible in the removal step C)—if this is performed—to quite overwhelmingly condense out the $C_3$ and/or $C_4$ hydrocarbons, and only a very small portion of the $C_3$ and/or $C_4$ hydrocarbons is discharged with the offgas stream c3 comprising hydrogen/low boilers.

Before the hydrocarbon condensation is performed, carbon dioxide can be removed from product gas stream b by gas scrubbing to obtain a carbon dioxide-depleted product gas stream b. The carbon dioxide gas scrubbing may be preceded by a separate combustion stage in which carbon monoxide is oxidized selectively to carbon dioxide.

For the $CO_2$ removal, the wash liquid used is generally sodium hydroxide solution, potassium hydroxide solution or an alkanolamine solution; preference is given to using an activated N-methyldiethanolamine solution. In general, before the gas scrubbing is performed, product gas stream c is compressed to a pressure in the range from 5 to 25 bar by single-stage or multistage compression.

It is possible to obtain a carbon dioxide-depleted product gas stream b having a $CO_2$ content of generally <100 ppm or even <10 ppm.

The liquid hydrocarbon condensate stream c2 obtained in the cooling and condensation step C) comprises generally from 20 to 60 mol % of alkane (II), from 20 to 60 mol % of alkene (III), from 0 to 20 mol % of low boilers and from 0 to 5 mol % of high boilers.

In the case of propane dehydrogenation, the liquid hydrocarbon condensate stream c2 obtained in the cooling and condensation step C) may comprise from 20 to 70 mol % of propane, from 20 to 60 mol % of propene, from 0 to 10 mol % of methane, from 0 to 10 mol % of ethane and ethene, and from 0 to 5 mol % of $C_4^+$ hydrocarbons.

When the autothermal alkane dehydrogenation is performed with feeding of air as the oxygenous gas, product gas stream b can be worked up and the alkane- and alkene-comprising mixture c2 can be obtained also as described below. First, steam is removed by condensation, by cooling product gas stream b and compressing it if appropriate to obtain a steam-depleted product gas stream b Subsequently, alkane and alkene are removed from uncondensible or low-boiling gas constituents by contacting product gas stream b with an inert absorbent and then desorbing the alkane and alkene dissolved in the inert absorbent to obtain a gaseous $C_3$ and/or $C_4$ hydrocarbon stream, and the offgas stream c3 comprising hydrogen and low boilers (in the case of the propane dehydrogenation, methane, ethane, ethene, nitrogen, carbon monoxide, carbon dioxide, with or without oxygen and with or without inert gases, in the case of n-butane dehydrogenation, additionally also propane and propene) is removed The workup of product gas stream b described can, in the case of the autothermal alkane dehydrogenation too, be performed correspondingly with feeding of pure oxygen and/or oxygen-enriched air as the oxygenous gas.

To this end, gas stream b is contacted with an inert absorbent in the absorption stage at 5-40 bar, preferably 8-20 bar, more preferably 10-15 bar, which absorbs the $C_3$ and/or $C_4$ hydrocarbons and also small amounts of the $C_2$ hydrocarbons in the inert absorbent and affords an absorbent laden with $C_3$ and/or $C_4$ hydrocarbons and an offgas c3 comprising the remaining gas constituents. These are essentially carbon oxides, hydrogen, inert gases and $C_2$ hydrocarbons, and methane. Small amounts of propane and propene and/or $C_4$ hydrocarbons may also still be present in stream c3, since the removal is generally not quite complete. In a desorption stage, the $C_3$ and/or $C_4$ hydrocarbons are released again from the absorbent.

Inert absorbents used in the absorption stage are generally high-boiling nonpolar solvents in which the $C_3$ and/or $C_4$ hydrocarbon mixture to be removed has a significantly higher solubility than the remaining gas constituents to be removed. The absorption can be effected by simply passing stream c through the absorbent. It can also be effected in columns. It is possible to work in cocurrent, countercurrent or crosscurrent. Suitable absorption columns are, for example, tray columns with bubble-cap trays, valve trays and/or sieve trays, columns with structured packings, for example fabric packings or sheet metal packings having a specific surface area of from 100 to 1000 $m^2/m^3$, such as Mellapak® 250 Y, and columns with random packing, for example with spheres, rings or saddles made of metal, plastic or ceramic as random packings. However, trickle and spray towers, graphite block absorbers, surface absorbers such as thick-film and thin-film absorbers, and bubble columns with and without internals, are also useful.

The absorption column preferably has an absorption section and a rectification section. To increase the enrichment of the $C_3$ and/or $C_4$ hydrocarbons in the solvent in the manner of a rectification, heat can then be introduced into the column bottom. Alternatively, a stripping gas can be fed into the column bottom, for example of nitrogen, air, steam or propane/propene mixtures. For instance, the laden absorbent is contacted with the stripping gas stream in the rectification section of the absorption column. This strips $C_2^-$hydrocarbons out of the laden absorbent. A portion of the top product can be condensed and introduced back to the top of the column as reflux in order to restrict the solvent losses.

Suitable absorbents are comparatively nonpolar organic solvents, for example aliphatic $C_4$-$C_{18}$-alkenes, naphtha or aromatic hydrocarbons such as the middle oil fractions from paraffin distillation, or ethers with bulky groups, or mixtures of these solvents, to which a polar solvent such as 1,2-dimethyl phthalate may be added. Suitable absorbents are also esters of benzoic acid and phthalic acid with straight-chain $C_1$-$C_8$-alkanols, such as n-butyl benzoate, methyl benzoate, ethyl benzoate, dimethyl phthalate, diethyl phthalate, and also so-called heat carrier oils such as biphenyl and diphenyl ether, their chlorine derivatives and triarylalkenes. A suitable absorbent is a mixture of biphenyl and diphenyl ether, preferably in the azeotropic composition, for example the commercially available Diphyl®. This solvent mixture frequently comprises dimethyl phthalate in an amount of from 0.1 to 25% by weight. Suitable absorbents are also butanes, pentanes, hexanes, heptanes, octanes, nonanes, decanes, undecanes, dodecanes, tridecanes, tetradecanes, pentadecanes, hexadecanes, heptadecanes and octadecanes, or fractions which have been obtained from refinery streams and comprise, as main components, the linear alkanes mentioned, Preferred absorbents are $C_8$-$C_{10}$ hydrocarbons; particular preference is given to $C_9$ hydrocarbons, especially nonanes.

For the desorption of the $C_3$ and/or $C_4$ hydrocarbons, the laden absorbent is heated and/or decompressed to a lower pressure. Alternatively, the desorption can also be effected by stripping, typically with steam, or in a combination of decompression, heating and stripping in one or more process steps. For example, the desorption can be performed in two stages, in which case the second desorption stage is performed at a lower pressure than the first desorption stage and the desorption gas of the second stage is recycled into the absorption stage. The absorbent regenerated in the desorption stage is recycled into the absorption stage. If appropriate, a portion of this absorbent stream which may comprise $C_4^+$ hydrocarbons is discharged, worked up and recycled, or discarded.

In one process variant, the desorption step is performed by decompressing and/or heating the laden absorbent. In a further process variant, stripping is effected additionally with steam.

The removal is generally not quite complete, so that small amounts or even only traces of the further gas constituents, especially of the low-boiling hydrocarbons, may still be present in the $C_3$ and/or $C_4$ hydrocarbon stream depending on the type of removal.

Subsequently, the desorbed $C_3$ and/or $C_4$ hydrocarbon stream may be cooled, in which case it may additionally be compressed in one or more further compression stages. This affords the liquid condensate stream c2 composed of $C_3$ and/or $C_4$ hydrocarbons. Stream c2 may also comprise small amounts of $C_2$ hydrocarbons. In addition, an aqueous condensate stream and in some cases further amounts of the offgas stream c3 may be obtained. The aqueous condensate stream is obtained generally when the dissolved gases are desorbed by stripping with steam.

The compression can in turn be effected in one or more stages. In general, compression is effected overall from a pressure in the range from 1 to 29 bar, preferably from 1 to 10 bar, to a pressure in the range from 12 to 30 bar. Each compression stage is followed by a cooling stage in which the gas stream is cooled to a temperature in the range from 15 to 80° C., preferably from 15 to 60° C. Subsequently, the compressed gas mixture is cooled to a temperature of from −10° C. to 60° C., preferably from −10° C. to 30° C. Any aqueous condensate stream present can be removed from the liquid $C_3$ and/or $C_4$ hydrocarbon stream in a phase separation apparatus.

The above-described absorption stage can also be performed as follows:

The absorbent used in the absorption column is the same organic acid which is reacted with the corresponding alkene in the esterification zone. In that case, it is possible to dispense with the above-described desorption step. The absorbent laden with $C_3$ and/or $C_4$ hydrocarbons, i.e. in this case the organic acid (e.g. formic acid or acetic acid), can then, if appropriate after further heating and/or compression, be conducted directly into the esterification zone. The absorbent feed used into the absorption column may in this case be the organic acid removed from the removal step (G) downstream of the ester hydrolysis zone. In that case, this organic acid is not recycled directly into the esterification zone but rather into the absorption stage and from there, laden with the $C_3$ and/or $C_4$ hydrocarbons, into the esterification zone.

The removal step within process part C) can but does not have to be performed. As described above, though, at least a compression of product gas stream b is always performed. For example, if the alkane dehydrogenation is not performed with feeding of an oxygenous gas nor in the presence of steam, the resulting dehydrogenation gas mixture b which, in the case of propane dehydrogenation, consists essentially of propane, propene, hydrogen and low boilers, and, in the case of n-butane dehydrogenation, essentially of butane, 1-butene, 2-butene, hydrogen and low boilers, can be fed directly into the esterification zone without preceding removal of the $C_3$ and/or $C_4$ hydrocarbons, and contacted with the organic acid. When product gas stream b comprises steam, since the dehydrogenation has been carried out with feeding of oxygen and/or with feeding of steam, a removal of steam alone—for example by condensation as described above under C)—may be sufficient, and the remaining mixture comprising $C_3$ and/or $C_4$ hydrocarbons, hydrogen and low boilers may be reacted in gaseous or liquid form with the organic acid. The presence of carbon oxides and further inert gases (atmospheric nitrogen) also do not fundamentally disrupt the esterification reaction.

The residual gas stream c3 can be and is preferably predominantly recycled into dehydrogenation stage A). A substream is removed and discharged from the process in order to prevent enrichment of secondary components. This substream can be incinerated or sent to a process stage for recovery of alkane/alkene present therein. The recovery can be performed as an absorption or adsorption, as a membrane separation or rectification.

A substream of the residual gas stream c3 can also be sent to the esterification step D).

The hydrocarbon phase c2 can be fed to the esterification stage D) directly or after further pressure increase. The aqueous condensate stream c1 can be discharged from the process or conducted into the ester hydrolysis stage (process part F)).

In a process stage D), product gas stream b or—if the separation step is performed in process stage C)—the phase c2 comprising the alkane (II) and the alkene (III) and, if appropriate, residual gas stream c3, or, if the absorption step is performed with the organic acid as described above, the organic acid laden with $C_3$ and/or $C_4$ hydrocarbons, is reacted with an organic acid (IV) in an esterification zone to obtain a product gas mixture d comprising the corresponding alkyl ester (V) (isopropyl ester and/or 2-butyl ester) of the organic acid (IV) and unconverted alkane (II).

The esterification can be performed in the liquid phase or biphasically (with regard to the reactants) as a gas/liquid reaction.

The esterification is generally performed at a pressure of from 10 to 100 bar and at a temperature of from 50 to 250° C. In general, the organic acid, based on alkene, is used in amounts of 0.5-50 mol, per mole of alkene, preferably in stoichiometric excess, preferably in amounts of 1.1-6 mol, more preferably 1.2-2.5 mol per mole of alkene. In general, from 50 to 90% of the alkene reacts to give the corresponding alkyl ester. In addition, unsaturated secondary components present in product gas stream b and/or in stream c2 can react to give alkyl esters. These can be removed by distillation directly in the workup steps which follow. The alkanes present in stream b and/or c2, by their nature, do not react in the esterification stage D) and leave the esterification stage D) together with the alkene unconverted in the esterification in stream d in the case of operation of the esterification stage D) in homogeneous liquid phase, or as an additional stream d2 in the case of operation of the esterification stage D) in gas-liquid mode. This stream may, in addition to alkane and alkene, also comprise small amounts of the ester formed and water, and the low boilers already present in stream c2.

The esterification stage D) is operated in gas-liquid mode, it may comprise two zones, a reaction zone and a rescrubbing zone. The aim of the reaction zone is a maximum conversion of the acid with the alkene. In the rescrubbing zone, addition of water largely frees gas stream d2 of acid residues. This allows corrosion problems in other plant parts when stream d2) is recycled to be avoided.

The esterification can be performed in fixed bed reactors in trickle mode or in fluidized bed mode. In principle, the organic acid and the alkene-containing stream can be conducted in co- or countercurrent, but also in crosscurrent. Preference is given to connecting a plurality of catalyst beds in a battery, if appropriate with intermediate feeding of the acid and/or of the alkene-containing stream. Preference is given to using a battery of 2-5, more preferably 2-3 different reaction zones. The heat of reaction released can be removed by internal heat exchange surfaces. A method with an external circulation system, in which a heat exchanger for removing the heat of reaction is mounted, is also possible. The adjustment of the circulation rate allows the axial temperature profile in the reactor to be adjusted virtually as desired. Alternatively, the esterification can also be performed in bubble columns or jet loop reactors. A particular embodiment is the tubular reactor in fluidized bed mode, which is operated in a controlled manner at the fluidization point of the catalyst (so-called floating bed method), with external heat exchanger and two reactors in a battery.

In the rescrubbing zone, addition of water removes acid residues. In apparatus terms, this zone corresponds to an absorption column which can be designed separately as a dedicated apparatus or integrated into the fixed bed reactor. The internals used may be trays, structured packings or random packings. The amount of the scrubbing water is selected such that the amount of acid residue in gas stream d2 is <50 ppm, preferably <<10 ppm, more preferably <<1 ppm. A typical ratio of amount of scrubbing water: amount of acid to be removed to achieve <1 ppm of acid is in the range from 1 kg/kg to 20 kg/kg. The scrubbing water laden with acid residues can be used in process stage F) for ester hydrolysis.

Suitable heterogeneous esterification catalysts are acidic ion exchange resins, especially those composed of sulfonated polystyrene crosslinked with divinylbenzene. These catalysts may have different pore structures—a distinction is drawn between microporous, gel-type and macroporous catalysts. It is also possible for electronegative radicals, for example chlorine or fluorine, to be bonded to the aromatic rings of the polystyrene. Suitable catalysts of this type are, for example, Amberlyst 15, 16, 36, 39, 40, 46, 48, 70, 119, 139 Lewatit K1131, K1221, K1461, K2420, K2629, K2649, Purolite CT169, CT175, CT275, Diaion RCP145H. Particular preference is given to those catalysts which comprise a high content of acidic groups, for example Amberlyst 35, 36, 40, 49, 119, Lewatit K2649, Purolite CT275. The catalysts mentioned here are typically obtainable in dry or in aqueous form. Both forms are suitable; in the case of the water-containing catalysts, the water is displaced by washing with the organic acid. A group of catalysts related to the acidic ion exchange resins derives from sulfonated polycondensed aromatics or graphitic carbon. Such materials are formed, for example, by sulfonating polycyclic aromatics, for example naphthalene or anthracene, under conditions which lead to condensation of the aromatics. A similar process proceeds from the carbonization of organic material, for example of sugars, under anaerobic conditions. The corresponding residues are then sulfonated. A further group of organic heterogeneous catalysts derives from ionic liquids which are adsorbed onto suitable support materials. In addition to the polymeric ion exchange resins, suitable catalysts are also a series of inorganic catalysts such as acidic metal oxide catalysts or acidic zeolites. The acidic metal oxide catalysts include in particular sulfated zirconium oxide and zirconium tungstate and/or titanium tungstate systems. This group of catalysts also includes the water-insoluble acidic salts of the heteropolyacids, for example of tungsto- or molybdophosphoric acid or of tungstosilicic acid. Such insoluble salts form from these acids with metal cations with large ionic radii, for example $K^+$, $Rb^+$, $Cs^+$, $NH_4^+$ or $Ag^+$. In these salts, typically 10-90 mol %, in particular 40-85 mol %, of the acidic sites have been exchanged for cations. A further group of catalysts is derived from heteropolyacids or salts thereof, which are adsorbed on an inert support material, for example silica gel, alumina or activated carbon. The suitable zeolite catalysts include those of the beta-zeolite, the faujasite, the mordenite and the ZSM-5 zeolite structure type. In addition to the zeolite structure, the ratio of the Si/Al atoms (the modulus) in the zeolite structure is crucial for the catalytic activity of the zeolite. Suitable zeolites for the process according to the invention are those which have a modulus between 2 and 500, in particular between 3 and 200 and most preferably between 5 and 100. The inorganic catalysts described here are typically activated thermally, i.e. the materials are calcined at temperatures between 50 and 900° C., preferably between 90 and 500° C.

The esterification reaction can also be effected under homogeneous catalysis. Suitable catalysts for this purpose are mineral acids, especially sulfuric acid, sulfonic acids or the free heteropolyacids, and their acidic soluble salts or acidic ionic liquids.

Preference is given to esterifying in the presence of heterogeneous catalysts. Preferred heterogeneous catalysts are acidic ion exchange resins, the acidic K, Cs or ammonium salts of the heteropolyacids, and beta-zeolites and faujasites. Particular preference is given to ion exchange resins.

Preferred organic acids (IV) are formic acid and acetic acid, which react with propene to give isopropyl formate and isopropyl acetate respectively, and with butenes (1-butene and 2-butene) to give 2-butyl formate and 2-butyl acetate respectively.

In process stage E), a gas stream e1 comprising the unconverted alkane (II) (propane and/or n-butane) is removed from product mixture d of the esterification, and is recycled into the dehydrogenation zone if appropriate. To this end, product mixture d of the esterification is generally decompressed to remove a gas stream e1 comprising propane and/or n-butane and to obtain a product mixture e2 comprising the alkyl ester (V) Gas stream e1 can be combined with gas stream d2 of the rescrubbing zone in process part D and they can be fed together to dehydrogenation zone B.

In general, product mixture d is decompressed from a pressure in the range from 20 to 60 bar to a pressure in the range from 2 to 10 bar. Any low boilers such as ethane, ethene, methane, carbon oxides and inert gases present in product mixture d are removed together with the propane and/or n-butane. The gas stream e1 comprising the alkane (II) is preferably recycled into the alkane dehydrogenation.

The gas stream e1 comprising the alkane (II) may also comprise low boilers such as ethane, ethene, methane, carbon oxides and inert gases, and also hydrogen. In general, it comprises low boilers with or without hydrogen when the above-described (optional) removal of low boilers and hydrogen (residual gas stream c3) has not already been effected in step C). From the gas stream e1, a substream can be removed and discharged from the process in order to prevent accumulation of secondary components. This substream can be incinerated or sent to a process stage for recovering alkane/alkene present therein. The recovery can be performed as an absorption or adsorption, as a membrane separation or rectification. Hydrogen present in the stream may be recovered, for example, by pressure swing adsorption. Both the recovered alkane/alkene and the recovered hydrogen may be recycled into the dehydrogenation. It is also possible to discharge the entire stream e1 from the process or send to the process stage for recovering alkane/alkene or hydrogen present therein.

In order to achieve better separation between alkene/alkane on the one hand and the ester/acid mixture on the other than in the case of pure decompression, a distillation and/or rectification can additionally be performed. For such a separation with a reflux ratio between 0.2 and 1.5, typically between 10 and 20 theoretical plates are required. It is possible here to use either tray columns, for example bubble-cap tray columns, and columns with random packing or columns with structured packing.

The product mixture d may also be decompressed from a pressure in the range from 20 to 60 bar to a pressure of generally from 2 to 45 bar, for example from 10 to 40 bar, or, in a specific variant, from 25 to 32 bar. The streams e1 and e2 present after the decompression may be worked up as described below using two columns K1 and K2.

It is possible to perform various variants of this workup. The variants I are notable in that the C3 components (propane and propene) are removed "sharply", only a very small amount of propane and propene being present in the bottom effluent (corresponds to stream e2) (for example approx. 100-1000 ppm by mass). The advantage of these variants is that only a very small amount of, if any, C3 hydrocarbons get into the subsequent steps F) and G). When the C3 components are not removed sharply, as corresponds to the variant II described below, this can entail a higher level of process complexity in stages F) and G).

In one variant Ia, the gas stream e1 present after the decompression is fed to a first column K1. The pressure in this column is equal to or only slightly lower than the pressure of the feed stream. The column K1 is preferably the pure rectifying section of a conventional column, i.e. it does not have an evaporator but has a condenser, and the feed is preferably at the bottom of the column. The liquid stream e2 present after the decompression is fed to the second column K2. The pressure of the column K2 is significantly below the pressure of the column K1. Typical pressures are, for example, 30 bar for K1 (all pressures absolute) and 1.5 bar for K2. In general, the pressure in K1 is from 10 to 40 bar, preferably from 25 to 32 bar, and, in K2, from 1 to 5 bar, preferably from 1.3 to 2 bar. The bottom draw of column K1 is likewise fed to column K2. The two top draw streams of the columns K1 and K2 correspond to stream e1 and can be used further or worked up further as described above. In this case, the top draw of the second column K2 is preferably recycled directly into the dehydrogenation, for which a compressor is optionally used.

In a further variant Ib, the procedure is as described under variant Ia, except that the pressure of column K2 here is higher (typical values, for example, K1=30 bar, K2=5 bar). In general, the pressure in K1 is from 10 to 40 bar, preferably from 25 to 32 bar, and that in K2 from 2.5 to 7 bar, preferably from 4 to 6 bar. This variant has the advantage that no compressor is required.

In a further variant Ic, the procedure is as described under variant Ia, with the difference that the condenser temperature of the column K2 is higher (for example approx. 40° C.). In general, this temperature is from 30 to 50° C., preferably from 37 to 45° C. As a result, the top draw stream of column K2 still comprises large proportions of alkyl esters and consequently cannot be recycled directly to the dehydrogenation. This stream is therefore compressed to the pressure of column K1 and sent to column K1. In this variant, only the top draw stream of column K1 corresponds to the stream e1 and can be used further or worked up further as described above. In general, the pressure in K1 is from 10 to 40 bar, preferably from 25 to 32 bar, and, in K2, from 1 to 5 bar, preferably from 1.3 to 2 bar.

In a further variant II, the procedure is as described under variant Ib, except that larger amounts of C3 components (propane and propene) are permitted in the bottom effluent of the column K2 (for example approx. 1-2% by mass), such that the bottom temperature is limited to approx. 100-110° C. and increased material requirements on evaporator and bottom part of the column K2 do not result. The pressure in the column K1 is generally from 10 to 40 bar, preferably from 25 to 35 bar; the pressure in the column K2 is generally from 2.5 to 7 bar, preferably from 4 to 6 bar.

It is optionally also possible to treat recycle stream d2 in the same way if it still comprises relatively large amounts of ester. Here too, preference is given to distillative purification of the stream. This can be done in a separate column, or alternatively together with the treatment of stream d in a common column. This can be followed by fine purification by adsorption, absorption, gas scrubbing or catalytic purification stages.

The product mixture e2 comprising the alkyl ester (V) (consisting essentially of the alkyl ester (V) and of the organic acid (IV), for example of isopropyl acetate and acetic acid) can be worked up further before stream e2 is conducted into process stage F). In a distillation column, the organic acid (IV), for example acetic acid, can be removed from the alkyl ester (V), for example isopropyl acetate. The organic acid (IV), for example acetic acid, can be obtained as the bottom product and recycled into the esterification stage. The alkyl ester (V), for example isopropyl acetate, can be obtained as the top product and conducted further into process stage F). Examples of suitable process parameters in the case of the separation of acetic acid and isopropyl acetate are a pressure of up to 2 bar (all pressures absolute) and a reflux ratio of from 0 to 3. The removal of the organic acid positively influences the reaction equilibrium in the hydrolysis reactor of process stage G). This allows a higher hydrolysis conversion to be enabled with the additional consequence that the recycle streams (water=stream h3; isopropyl acetate=stream i1) are greatly reduced. Owing to the significantly smaller recycle streams, capital and energy demands, for example of the apparatus (2), (3), (4) and (5) described below, are reduced. As a result of the removal of the organic acid (IV) described before the hydrolysis stage F) is performed, addition stage D) and hydrolysis stage F) are additionally decoupled.

In a process step F), the product mixture e2 comprising the alkyl ester (V) is reacted with water in an ester hydrolysis zone to give a product mixture f comprising the alkanol (I) (isopropanol and/or 2-butanol) and the organic acid (IV). In a process stage G), the alkanol (I) is removed from product mixture f and the organic acid (IV) is recovered. The organic acid (IV) is generally recycled into the esterification stage D), or it is conducted as an absorbent into the absorption stage for removing alkene and alkane from gas phase c3.

In this stage, product mixture f can be separated into a stream g1 comprising the acid and a stream g2 comprising the alkanol (I) and the alkyl ester (V). The alkyl ester can be removed by distillation from the alkanol stream g2 and recycled into the ester hydrolysis zone. Depending on the phase equilibria, the alkanol (i) can be removed from product mixture f by simple distillation or by azeotropic rectification with use of azeotroping agents (for example benzene, cyclohexane or diisopropyl ether in the case of isopropanol), by extractive distillation using an extractant (for example ionic liquids or acetic acid) and by membrane processes (pervaporation or vapor permeation).

The esterification can be performed either under homogeneous or heterogeneous catalysis. Suitable catalysts for the ester hydrolysis are in principle the above-described catalysts, which are also used in the esterification reaction. Preferred heterogeneous catalysts are ion exchange resins. Preferred homogeneous catalysts are sulfuric acid or heteropolyacids.

The ester hydrolysis zone can be configured as a reactor or as a reactive distillation column. A combination of reactor and reactive distillation column is also possible.

Preference is given to performing the ester hydrolysis with a substoichiometric amount of water. This allows the organic acid (IV) to be recovered essentially in concentrated form and it does not need to be concentrated any further before it is recycled into the esterification stage D).

Ester hydrolysis and distillation can be performed in separate process steps. In one variant of the process according to the invention, the mixture e2 comprising the alkyl ester (V) is reacted with water in an ester hydrolysis reactor to give a product mixture comprising the alkanol (I), the organic acid (IV), the alkyl ester (V) and water, and this mixture is then separated in at least 2 distillation columns connected in series, if appropriate in conjunction with a dividing wall column.

In the case of the heterogeneously catalyzed ester hydrolysis, the ester hydrolysis reactor can be configured as a fixed bed reactor, trickle bed reactor, fluidized bed reactor or suspension reactor. In the case of the fluidized bed reactor, the catalyst can be operated in a controlled manner at the fluidization point (so-called floating bed method). In the case of the homogeneously catalyzed ester hydrolysis, the reactor can, for example, be configured as a stirred tank reactor or tubular reactor. When the ester hydrolysis is performed homogeneously, the catalyst is generally removed together with the organic acid in process step G), generally via the bottom draw stream of the first distillation column. In this case, the catalyst can be removed before the organic acid is recycled into the esterification stage D), and the catalyst removed can be recycled into the ester hydrolysis reactor. The catalyst can be removed thermally in an evaporator or in a multistage distillation column, and also in a phase separator, or else by combination of phase separation and thermal separation. When the same homogeneous catalyst as for the esterification is used for the ester hydrolysis, it is possible to dispense with separate removal of the catalyst. For this process variant, heteropolyacids or sulfuric acid are particularly suitable.

For example, in a first specific embodiment of the process according to the invention, the organic acid used is acetic acid and an isopropyl acetate-comprising product mixture e2 is obtained, and, in step F), the isopropyl acetate-comprising product mixture e2 is reacted with water in an ester hydrolysis reactor to give a product mixture f comprising isopropanol, acetic acid, isopropyl acetate and water, and, in step G), product mixture f is separated in a first distillation column (1) into a stream g1 essentially consisting of acetic acid and a stream g2 comprising isopropyl acetate, isopropanol and water, and stream g2 is separated in a second distillation column (2) into a stream h1 comprising isopropyl acetate and isopropanol, and a stream h2 essentially consisting of isopropanol and water, and stream g1 is recycled into the esterification zone. This variant is shown in FIG. 1.

In a specific variant, the separation of the product mixture f into a stream g1 consisting essentially of acetic acid and a stream g2 comprising isopropyl acetate, isopropanol and water can be combined with an additional hydrolysis step. To this end, the distillation column (1) can be equipped with a side reactor which comprises the hydrolysis catalyst, or the distillation column (1) can be designed as a reactive distillation column by virtue of at least one column section being equipped with trays or structured packings which comprise the hydrolysis catalyst, or downstream of the distillation column (1), a substream of the stream g2 can be conducted through a reactor comprising the hydrolysis catalyst and recycled into the distillation column (1). The process parameters for the additional hydrolysis reactor are, for example, a pressure of from 2 to 10 bar and a temperature of from 60 to 130° C.

The additional hydrolysis reactor entails the following advantages: since the reaction conversion in the hydrolysis reactor (process step F) is limited by the reaction equilibrium, stream f is virtually at the reaction equilibrium. As a result of the acetic acid removal in distillation column (1), a further hydrolysis conversion becomes possible, which can be implemented in the additional hydrolysis reactor. As a consequence of the additional hydrolysis conversion, the recycle streams (water=stream h3; isopropyl acetate=stream i1) are reduced, and correspondingly also the capital cost and energy demand of the apparatus (2), (3), (4) and (5) described below.

In a further column (4), isopropanol can be removed as the distillate from stream h1 so as to obtain a stream i1 which consists essentially of isopropyl acetate and is recycled into the ester hydrolysis reactor (10). The water present in stream g2 can be removed by azeotropic distillation, comprising two distillation columns (referred to hereinafter as the second (2) and third column (3)) and a phase separator (5), using an azeotroping agent, for example benzene or diisopropyl ether, and recycled as stream h3 into the ester hydrolysis reactor (10). When diisopropyl ether is obtained as a by-product in the ester hydrolysis, the azeotroping agent used in the water removal is preferably diisopropyl ether.

The ester hydrolysis is performed generally at a pressure of from 1 to 10 bar, preferably from 2 to 5 bar, and a temperature of from 50 to 150° C., preferably from 80 to 120° C. Preference is given to working in the presence of acidic ion exchanger as the catalyst. Water can be used in a stoichiometric deficiency or excess; it is generally used in stoichiometric deficiency based on isopropyl acetate, preferably in amounts of from 0.5 to 0.9 mol of water per mole of isopropyl acetate. Preference is given to effecting the ester hydrolysis reaction in a fluidized bed reactor in floating bed mode.

The resulting product mixture f comprises, for example, from 5 to 20% by weight of isopropanol, from 10 to 50% by weight of acetic acid, from 30 to 70% by weight of isopropyl acetate and from 5 to 15% by weight of water. Stream g1, which is generally obtained as the bottom draw stream of the first column (1), comprises, for example, from 90 to 100% by weight of acetic acid and may additionally also comprise from 0 to 5% by weight of isopropyl acetate and from 0 to 5% by weight of isopropanol. Stream g2, which is generally obtained as the top draw stream of the first column (1), comprises, for example, from 40 to 70% by weight of isopropyl acetate, from 10 to 80% by weight of isopropanol and from 0 to 20% by weight of water. Stream h1, which is generally obtained as the bottom draw stream of the second column (2), comprises, for example, from 60 to 90% by weight of isopropyl acetate and from 5 to 30% by weight of isopropanol and from 0 to 5% by weight of acetic acid, and stream h2, which is generally obtained as the top draw stream of the second column (2), comprises, for example, from 30 to 60% by weight of isopropyl acetate, from 5 to 15% by weight of water and from 10 to 30% by weight of isopropanol. In addition, stream h2 may also comprise up to 50% by weight of the azeotroping agent and traces of acetic acid.

The stream h3 obtained as the bottom draw stream of the third column (3) comprises preferably at least 95% by weight of water, and stream h4, which is generally obtained as the top draw stream of the third column (3), comprises, for example, from 5 to 15% by weight of isopropyl acetate, from 15 to 50% by weight of water and from 30 to 70% by weight of isopropanol. In addition, stream h4 may also comprise up to 5% by weight of azeotroping agent and traces of acetic acid. Stream i1, which is generally obtained as the bottom draw stream of a further (fourth) column (4) comprises preferably at least 90% by weight of isopropyl acetate, up to 5% by weight of acetic acid and up to 5% by weight of isopropanol, and stream i2, which is generally obtained as the top draw stream of the fourth column (4), comprises preferably at least 98% by weight of isopropanol. In addition, stream i2 may also comprise up to 2% by weight of isopropyl acetate and traces of azeotroping agent and water.

In the phase separator (5), the top draw streams h4 and h2 with addition of an azeotroping agent (benzene) are separated into an aqueous phase and an organic phase. The aqueous phase is introduced as reflux to the third column (3) and comprises preferably at least 70% by weight, up to 10% by weight of isopropyl acetate, up to 20% by weight of isopropanol and traces of azeotroping agent. The organic phase is introduced as reflux to the second column (2) and comprises preferably at least 40% by weight of isopropyl acetate, up to 10% by weight of water, from 10 to 40% by weight of isopropanol and from 10 to 50% by weight of azeotroping agents, and also traces of acetic acid.

The first column (1) has generally from 10 to 30 theoretical plates and is operated at a pressure of from 0.5 to 2 bar. The second column (2) has generally from 25 to 50 theoretical plates and is operated at a pressure of from 0.5 to 2 bar. The third column (3) has generally from 1 to 15 theoretical plates and is operated at a pressure of from 0.5 to 2 bar. The fourth column (4) has generally from 40 to 70 theoretical plates and is operated at a pressure of from 5 to 10 bar.

Figure 2:
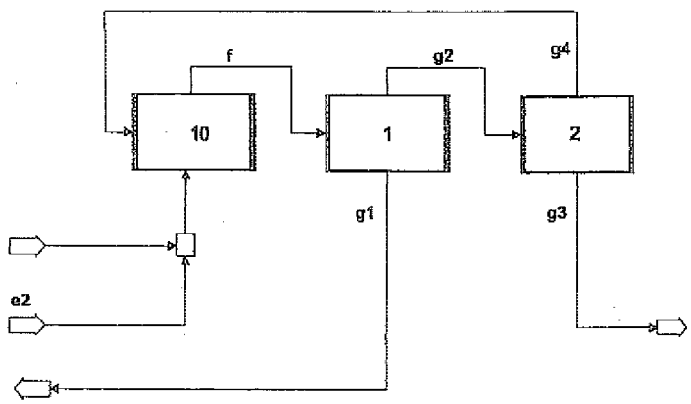

In a second specific embodiment of the process according to the invention, the organic acid used is formic acid and an isopropyl formate-comprising product mixture e2 is obtained, and, in step F), the isopropyl formate-comprising product mixture e2 is reacted with water in an ester hydrolysis reactor (10) to give a product mixture f comprising isopropanol, formic acid, isopropyl formate and water, and, in step G), product mixture f is separated in a first distillation column (1) into a stream g1 comprising formic acid and water, and a stream g2 comprising isopropyl formate, isopropanol and water, and stream g2 is separated in a second distillation column (2) into a stream g4 comprising isopropyl formate, water and isopropanol, and a stream g3 essentially consisting of isopropanol and stream g1 are recycled into the esterification zone, and stream g4 into the ester hydrolysis reactor (10). g3 is generally obtained as the bottom draw stream or gaseous side draw stream. In addition, water can be removed from formic acid in stream g1, and thus only the concentrated formic acid can be conducted back into the esterification zone, which achieves higher space-time yields and allows the low-formic acid water stream to be conducted back into the ester hydrolysis reactor. This variant is shown in FIG. 2.

The ester hydrolysis is performed generally at a pressure of from 1 to 10 bar, preferably from 2 to 5 bar, and a temperature of from 50 to 150° C., preferably from 80 to 120° C. Preference is given to working in the presence of acidic ion exchanger as the catalyst. Water is used generally in a stoichiometric deficiency based on isopropyl formate, preferably in amounts of from 0.5 to 0.9 mol of water per mole of isopropyl formate. If appropriate, water can also be added in stoichiometric excess.

Product mixture f comprises, for example, from 10 to 25% by weight of isopropanol, from 15 to 40% by weight of formic acid, from 20 to 60% by weight of isopropyl formate and from 5 to 20% by weight of water.

Stream g1, which is generally obtained as the bottom draw stream of the first column (1), comprises generally a mixture of, for example, from 80 to 95% by weight of formic acid and from 5 to 20% by weight of water. Stream g2, which is generally obtained as the top draw stream of the first column (1), comprises, for example, from 50 to 80% by weight of isopropyl formate, up to 10% by weight of water and from 20 to 40% by weight of isopropanol. Stream g4, which is generally obtained as the top draw stream of the second column (2), comprises a mixture of, for example, from 70 to 90% by weight of isopropyl formate, up to 15% by weight of water and from 5 to 15% by weight of isopropanol. Stream g3, generally as the top draw stream or gaseous side draw stream of the second column (2), consists preferably to an extent of at least 98% by weight of isopropanol and may additionally also comprise water in amounts of up to 2% by weight.

The first column (1) has generally from 30 to 60 theoretical plates and is operated at a pressure of from 0.5 to 3 bar. The second column (2) has generally from 30 to 60 theoretical plates and is operated at a pressure of from 0.5 to 1 bar.

Figure 3:
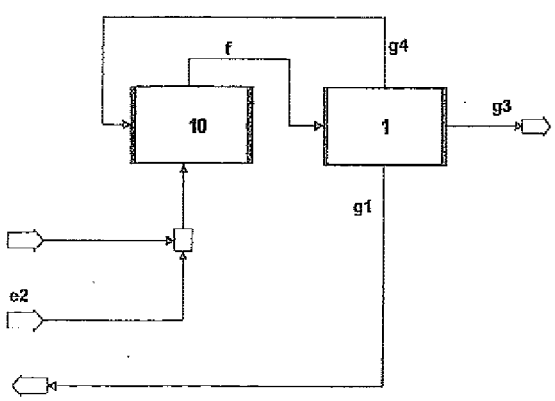

In a third specific embodiment of the process according to the invention, in step F), the isopropyl formate-comprising product mixture e2 is reacted with water in an ester hydrolysis reactor (10) to give a product mixture f comprising isopropanol, formic acid, isopropyl formate and water, and, in step G), product mixture f is conducted into a dividing wall distillation column (1) on one side of the dividing wall and separated into a stream g1 comprising formic acid and water, a distillate stream g4 comprising isopropyl formate, water and isopropanol, and a side stream g3 on the far side of the dividing wall essentially consisting of isopropanol, and the bottom stream g1 is recycled into the esterification zone and stream g4 into the ester hydrolysis reactor (10). The composition of the streams g1, g3 and g4 obtained is preferably the same as in the case of connection of two separate columns. The dividing wall column (1) has generally from 10 to 30 theoretical plates in the preliminary column and from 30 to 60 theoretical plates in the main column, and is operated at a pressure of from 0.5 to 3 bar. This variant is shown in FIG. 3.

However, it is also possible to perform part of ester hydrolysis and distillation simultaneously in one and the same process step in a reactive distillation column, in which case the mixture formed by ester hydrolysis is simultaneously separated by distillation at least partly and the organic acid (if appropriate together with a homogeneous catalyst) is recovered. The reactive distillation column may be preceded upstream by a preliminary reactor.

The reactive distillation can be performed under homogeneous or heterogeneous catalysis. The reactive distillation column may comprise customary internals (for example structured packings, random packings, trays). Heterogeneous catalysts may be present in the form of catalytic internals, for example as catalytic structured packings or random packings, or as a suspension. In addition, accommodation of the catalyst in external vessels which are fed by a side stream of the reaction column is possible.

In one variant of the process according to the invention, the mixture e2 comprising the ester is reacted with water in a preliminary ester hydrolysis reactor to give a product mixture f comprising the alkanol (I), the organic acid (IV), the alkyl ester (V) and water, and a product mixture f2 composed of the alkanol (I) and the alkyl ester (V), and a stream f3 which is composed of the organic acid (IV) and is recycled into the esterification zone, are obtained from product gas mixture f in a reactive distillation column, and product mixture f2 is separated in a downstream (further) distillation column into a stream g1 composed of the alkanol (I) and the alkyl ester (V) and small amounts of water, and a stream g2 composed of the alkanol (I), stream g1 being recycled into the ester hydrolysis zone, preferably into the reactive distillation column.

Figure 4:
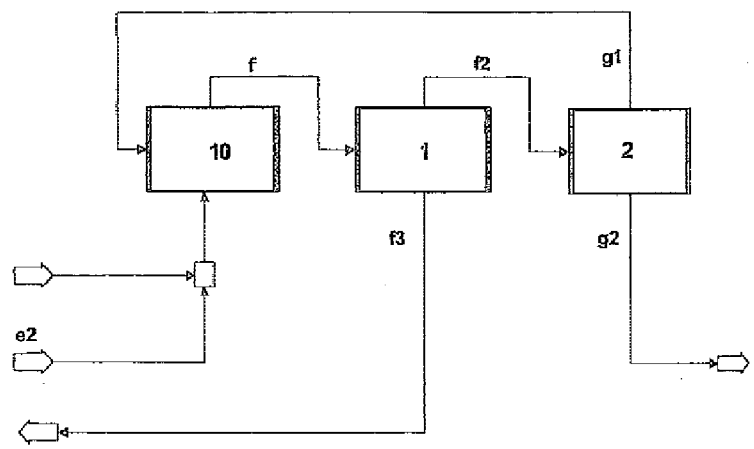

For example, in a fourth specific embodiment of the process according to the invention, in step F), the isopropyl acetate-comprising product mixture e2 is reacted with water in a preliminary ester hydrolysis reactor to give a product mixture f comprising isopropanol, acetic acid, isopropyl acetate and water, a product mixture f2 essentially consisting of isopropanol, isopropyl acetate and small amounts of water, and a stream f3 essentially consisting of acetic acid, are obtained from product gas mixture f in a reactive distillation column (1), and stream f3 is recycled into the esterification zone, and, in step G), product mixture f2 is separated in a distillation column (2) into a stream g1 essentially consisting of isopropanol, isopropyl acetate and small amounts of water, and a stream g2 essentially consisting of isopropanol. Stream g1 can be recycled into the ester hydrolysis reactor (10) or preferably into the reactive distillation column (1). This variant is shown in FIG. 4.

Product mixture f, which comprises, for example, from 5 to 20% by weight of isopropanol, from 10 to 90% by weight of acetic acid, from 10 to 80% by weight of isopropyl acetate and from 1 to 20% by weight of water is reacted further in the reactive distillation column (1) and simultaneously separated into a stream f2 which comprises, for example, from 30 to 80% by weight of isopropanol and from 10 to 70% by weight of isopropyl acetate and up to 10% by weight of water and is generally obtained as a top draw stream, and a stream f3 which consists preferably to an extent of at least 90% by weight of acetic acid, may additionally also comprise isopropyl acetate and isopropanol, and is generally obtained as the bottom draw stream.

In the reaction column, the catalytically active internals may be arranged either below or above the feed. In addition, further separating internals may be present at the top and in the bottom of the column. The feed is preferably below the reaction zone. The reaction column has generally from 30 to 80 theoretical plates and is operated at a pressure of from 1 to 6 bar. In addition to the feed f, water may be added above and below the reaction zone, and also into the reaction zone itself.

Stream g1, which is generally obtained as the top draw stream of the distillation column (2), comprises, for example, from 10 to 50% by weight of isopropanol and from 30 to 90% by weight of isopropyl acetate. Stream g2, which is generally obtained as the bottom draw stream or gaseous side draw stream of the distillation column (2), consists preferably to an extent of at least 98% by weight of isopropanol. In addition, it may also comprise isopropyl acetate, generally in amounts of up to 1% by weight. The distillation column (2) has generally from 10 to 50 theoretical plates and is operated at a pressure of from 0.01 to 1 bar.

The ester hydrolysis reactor (10) connected upstream of the reactive distillation column (1) can also be dispensed with. The advantage of the preliminary reactor in the heterogeneously catalyzed reactive distillation is that the amount of catalyst in the column here can be reduced, and the preliminary reactor additionally acts as a protective bed protecting from catalyst poisons.

Figure 5:
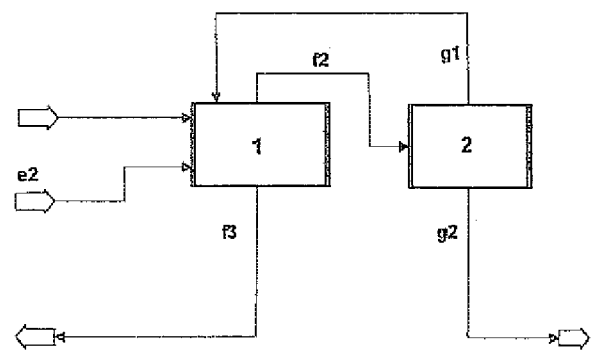

Thus, in a fifth specific embodiment of the process according to the invention, in step F), the isopropyl acetate-comprising product mixture e2 is fed with water directly into a reactive distillation column (1) and a product mixture f2 essentially consisting of isopropanol, isopropyl acetate and small amounts of water, and a stream f3 essentially consisting of acetic acid, are obtained from product mixture e2 in the reactive distillation column (1), and stream f3 is recycled into the esterification zone, and, in step G), product mixture f2 is separated in a distillation column (2) into a stream go essentially consisting of isopropanol, isopropyl acetate and small amounts of water, and a stream g2 essentially consisting of isopropanol, and stream g1 is recycled into the reactive distillation column (1). This variant is shown in FIG. 5.

The composition of streams f2, f3, g1 and g2 corresponds essentially to the method with upstream ester hydrolysis reactor.

In addition to the use of a heterogeneous catalyst for ester hydrolysis, it is likewise possible to use a homogeneous catalyst.

Figure 6:
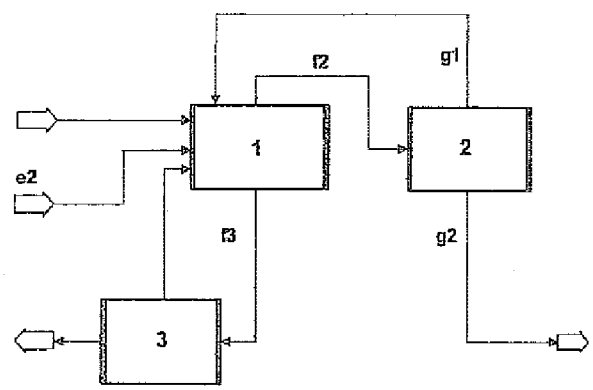

Thus, in a sixth specific embodiment of the process according to the invention in step F), the isopropyl acetate-comprising product mixture e2 is fed with water into a reactive distillation column (1) and a product mixture f2 essentially consisting of isopropanol, small amounts of water and isopropyl acetate, and a stream f3 essentially consisting of acetic acid and the homogeneous catalyst, are obtained from product mixture e2 in the reactive distillation column (1) and is recycled into the esterification zone, and, in step G), product mixture f2 is separated in a distillation column (2) into a stream g1 essentially consisting of isopropyl acetate water and isopropanol, and a stream g2 essentially consisting of isopropanol, and stream g1 is recycled into the reactive distillation column. This variant is shown in FIG. 6.

The catalyst can be removed from stream f3 thermally in an evaporator or a multistage distillation column and in a phase separator, or the combination of phase separator and thermal removal. The concentrated catalyst stream is recycled into the rectifying section of the reaction column, and the concentrated acetic acid is recycled back into the esterification stage.

The composition of streams f2, g1 and g2 corresponds essentially to the method with heterogeneously catalyzed reactive distillation. Stream f3, preferably consisting of acetic acid, may comprise up to 50% by weight of catalyst.

In the reaction column (1), conventional internals for distillation are present, Preferably present in the reaction zone are column trays, for example chimney trays, which allow the setting of defined residence times. In addition to internal column internals, it is possible for defined residence times additionally to be realised in an external vessel attached to the column, by means of drawing off a stream from the column by means of a side draw, passing it through the vessel and conducting it back into the column. The reaction column has generally from 30 to 100 theoretical plates and is operated at a pressure of from 1 to 6 bar. In addition to the feed e2, water can be added to the reaction zone.

In the fourth, fifth and sixth specific process variants described above, preference is given to using water in step F) in stoichiometric deficiency based on isopropyl acetate. Since water is converted virtually fully in the reaction column, this prevents the formation of aqueous-organic azeotropes (such as isopropanol-water, isopropanol-isopropyl acetate-water).

In the case of isopropyl formate too, the ester hydrolysis can be performed as a reactive distillation (with and without preliminary reactor).

Thus, in a seventh specific embodiment of the process according to the invention, the isopropyl formate-comprising product mixture e2 is reacted with water in an ester hydrolysis reactor (10) to give a product mixture f comprising isopropanol, formic acid, isopropyl formate and water, and a product mixture f2 essentially consisting of isopropanol and isopropyl formate, and a stream f3 essentially consisting of formic acid and water, are obtained from product mixture f in a reactive distillation column (1), and stream f3 is recycled into the esterification zone, and, in step G), product mixture 72 is separated in a distillation column (2) into a stream g1 essentially consisting of isopropanol and isopropyl formate and a stream g2 essentially consisting of isopropanol, and stream g1 is recycled into the ester hydrolysis reactor (10) or preferably in the reactive distillation column (1). This variant is likewise shown in FIG. 4.

Product mixture f, which comprises, for example, from 5 to 15% by weight of isopropanol, from 5 to 50% by weight of formic acid, from 20 to 70% by weight of isopropyl formate and from 1 to 15% by weight of water, is converted further in the reactive distillation column (1) and simultaneously separated into a stream f2 which comprises, for example, from 10 to 50% by weight of isopropanol and from 30 to 80% by weight of isopropyl formate and is generally obtained as the top draw stream, and a stream f3 which comprises, for example, from 60 to 85% by weight of formic acid and from 5 to 20% by weight of water, may additionally comprise isopropyl formate and is generally obtained as the top draw stream.

Stream g1, which is generally obtained as the top draw stream of the distillation column (2), comprises generally an azeotropic mixture composed, for example, of from 5 to 30% by weight of isopropanol and from 60 to 95% by weight of isopropyl formate. Stream g2, which is generally obtained as the bottom draw stream or gaseous side draw stream in the stripping section of the distillation column (2), consists preferably to an extent of at least 99% by weight of isopropanol. In addition, it may also comprise isopropyl formate, generally in amounts of up to 1% by weight. The distillation column (2) has generally from 10 to 30 theoretical plates and is operated at a pressure of from 0.1 to 1 bar.

In the seventh specific process variant described above, it is likewise preferred to use water in step F) in stoichiometric deficiency based on isopropyl formate. Since water is converted virtually fully in the reaction column, this prevents the formation of aqueous-organic azeotropes (for example isopropanol-water, isopropanol-isopropyl formate-water).

In the reaction column (1), the catalytic internals may be arranged either below or above the feed. In addition, further separating internals may be present at the top and in the bottom of the column. The feed is preferably below the reaction zone. The reaction column has generally from 30 to 80 theoretical plates and is operated at a pressure of from 1 to 6 bar.

The ester hydrolysis reactor (10) connected upstream of the reactive distillation column (1) can likewise be dispensed with. The downstream column (2) and the reaction column (1) can also be combined to give a reactive dividing wall column.

The invention is illustrated in detail by the examples which follows.

EXAMPLE 1

Figure 7:
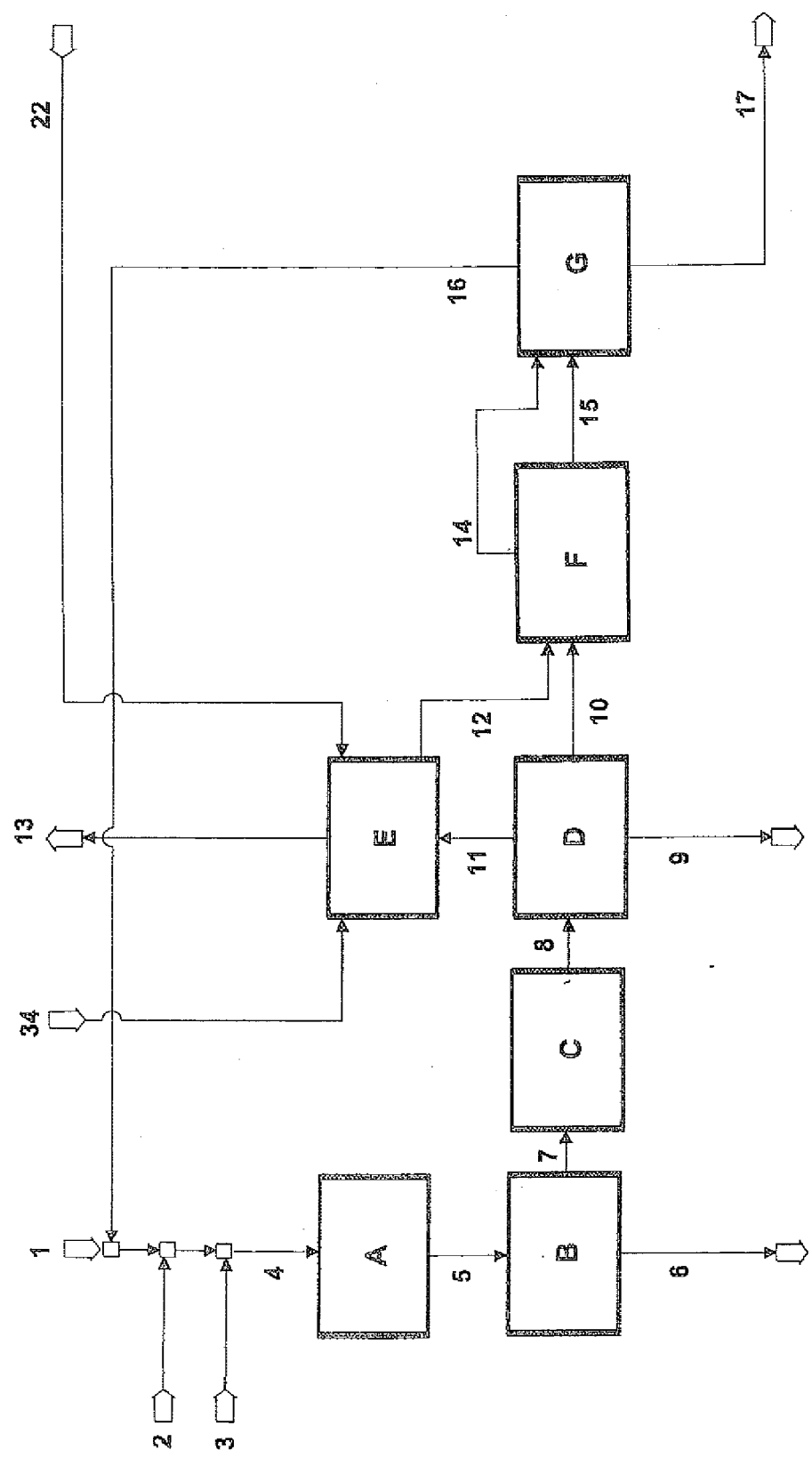
Figure 8:
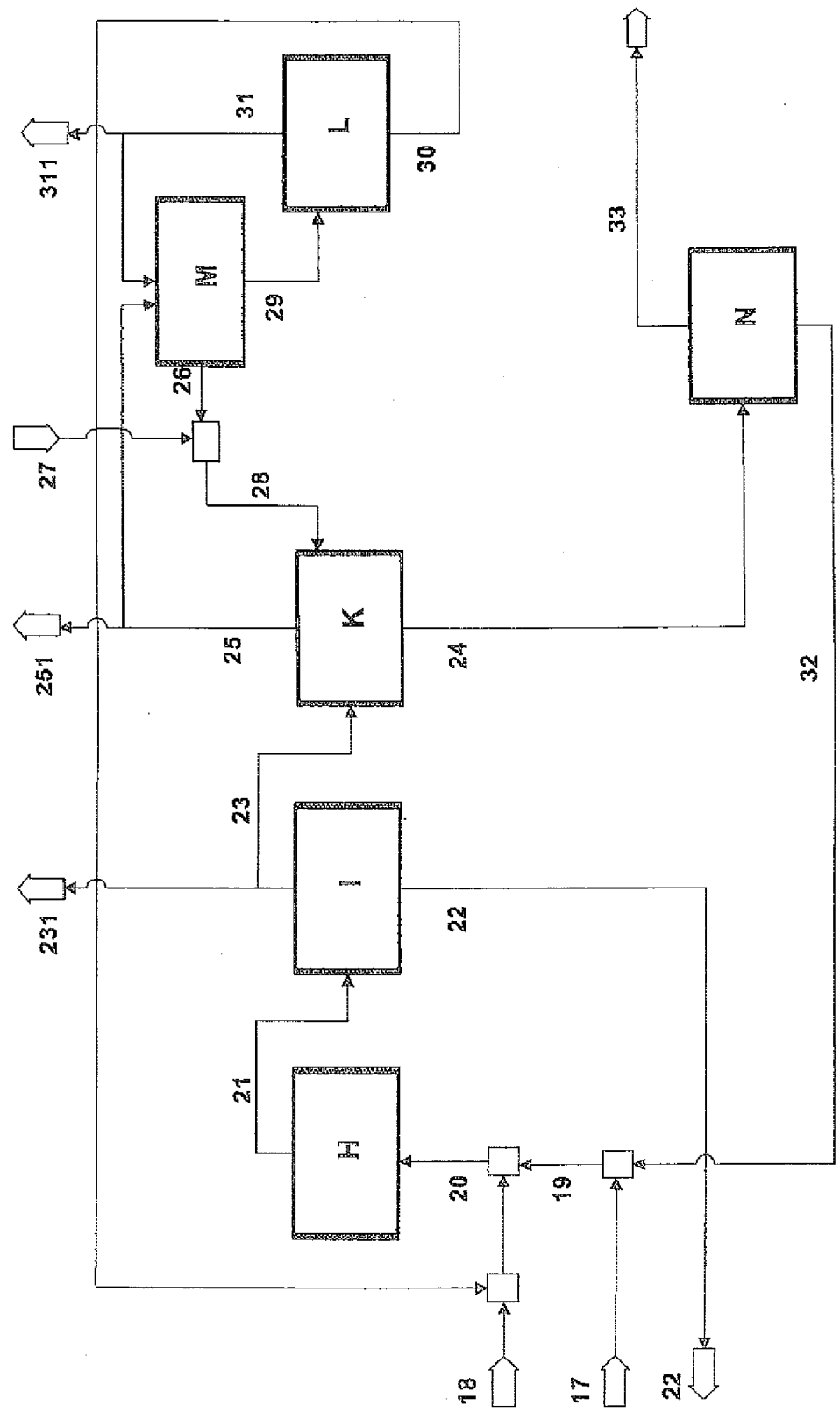

With the aid of the commercial simulation program Aspen-Plus, an integrated overall process for the production of isopropanol from propane was calculated by way of example. In this example, the process comprises stages A to N. These are shown with the accompanying streams in FIGS. 7 and 8. The calculated compositions of the individual streams can be taken from the table. The simulation calculation is based on a steady-state equilibrium model on the basis of measurements of vapor-liquid and liquid-liquid phase equilibria.

A propane-rich gaseous stream (4) is fed to the propane dehydrogenation reactor A. This is composed of the recycle stream (16) from the top of the rectification column G, which comprises essentially propane, and the feeds of fresh propane (1), water (2) and oxygen (3). The dehydrogenation gas mixture (5) at 590° C. leaving reactor A is cooled in stages in the cooling and condensation stage B to obtain an aqueous condensate stream (6). The product gas stream (7) is fed to the compression stage C in which it is compressed to 40 bar. The compressed stream (8) is separated in the phase separator D into three substreams. The gas stream (11) is fed to the absorption column E, the liquid propane- and propene-rich stream (10) to the esterification reactor F. Also obtained in the phase separator D is an aqueous stream (9). In the absorption column E, propane and propene are preferably dissolved in an absorbent and fed together with the absorbent as stream (12) to the esterification reactor F. The absorbent used is the acetic acid-rich stream (22) recycled from the bottom draw of the rectification column 1, which is supplemented with fresh acetic acid (34). The gas stream (13) can be discharged as offgas or else, if appropriate after an additional separation step, recycled back into the dehydrogenation reactor A. In the esterification reactor F, at 40 bar and 110° C., 90% of the propene supplied with streams (12) and (10) is reacted with acetic acid to give isopropyl acetate. For the calculation, a selectivity of 100% for isopropyl acetate is assumed. The two exit streams from the esterification reactor F, the gaseous stream (14) and the liquid stream (15), are fed to the rectification column G. The gaseous top draw stream (16) of column G is conducted into the propane dehydrogenation reactor A, and the liquid bottom draw stream (17) into the ester hydrolysis reactor H. In addition to this stream (17), water (18) and the two bottom draw streams (30) and (32) of the rectification columns L and N respectively are fed to the ester hydrolysis reactor H. In the ester hydrolysis reactor H, at 5 bar and 100° C., 20% of isopropyl acetate is converted to isopropanol at an assumed selectivity of 100%. The exit stream (21) from the ester hydrolysis reactor H is fed to the downstream rectification column I. The acetic acid-rich bottom draw stream (22) of the column I is recycled into the absorption column E. At the top condenser of the rectification column I, an offgas stream (231) composed of gases uncondensible under these conditions, and the remaining top draw stream (23), are conducted into the stripping column K. In the stripping columns K and L and the phase separator M, a heteroazeotropic rectification stage with benzene as the azeotroping agent is performed. In each case at the upper ends of the two columns K and L, an offgas stream composed of gases uncondensible under these conditions is drawn off (streams 251 and 311). The two remaining top draw streams (25) and (31) are conducted into the phase separator M. From the phase separator M, the upper liquid phase (26) is fed with the feedstream of fresh benzene (27) together as stream (28) to the top of the stripping column K, and the lower liquid phase (29) to the top of the stripping column L. The bottom draw stream (30) essentially comprising water from the stripping column L is recycled to the ester hydrolysis reactor H. The bottom draw stream (24) of the stripping column K is fed to the rectification column N. The bottom draw stream (32) of the column N, which comprises essentially isopropyl acetate, is recycled to the ester hydrolysis reactor H. At the top of the rectification column N, the desired product stream (33) is obtained with a content of 99.7% mass of isopropanol.

Table 1 below once again summarizes the individual stages A-N. The composition of the streams is reproduced by Table 2.

TABLE 1

Apparatus list

| Stage | Description |
|---|---|
| A | Dehydrogenation reactor; 2.5 bar; 590° C.; propane conversion: 35%; selectivity for propene: 95% |
| B | Cooling and condensation stage; 2.4 bar; end temperature 60° C. |
| C | Compression stage; end pressure 40 bar |
| D | Phase separator; 40 bar; 60° C. |
| E | Absorption column; 40 bar; absorbent feed at 40° C.; 30 theoretical plates |
| F | Esterification reactor; 40 bar; 110° C.; propene conversion: 90%; selectivity for isopropyl acetate: 100% |
| G | Rectification column; 5 bar; 13 theoretical plates, reflux ratio: 0.6 |
| H | Ester hydrolysis reactor; 5 bar, 100° C.; isopropyl acetate conversion: 20%; selectivity for isopropanol: 100% |
| I | Rectification column; 1 bar; 21 theoretical plates, reflux ratio: 0.5 |
| K | Stripping column; 1 bar; 35 theoretical plates |
| L | Stripping column; 1 bar; 3 theoretical plates |
| M | Phase separator; 1 bar; 40° C. |
| N | Rectification column; 7 bar; 60 theoretical plates, reflux ratio: 6.6 |

EXAMPLE 2

In a continuous autoclave with a reaction volume of 200 ml, at 110° C. and 40 bar, 16.9 g of propylene, 34.4 g of propane and 116.7 g of acetic acid per hour are reacted in the presence of 15.7 g of "Amberlyst 35 wet" as a catalyst. The effluent stream is decompressed, and the liquid and gaseous phase are analyzed separately by GC. At a propylene conversion of 90%, isopropyl acetate is obtained with a selectivity of over 96%.

The invention claimed is:

1. A process for preparing an alkanol (I) from its corresponding alkane (II), comprising:
   A) providing a starting gas stream (a) comprising said alkane (II);
   B) feeding said starting gas stream (a) into a dehydrogenation zone and dehydrogenating said alkane (II) to its corresponding alkene (III) to obtain a product gas stream (b) comprising said alkene (III), unconverted alkane (II), steam, hydrogen, and low boilers, and optionally high boilers;

TABLE 2

| Stream | | 1 | 2 | 3 | 4 | 5 | 6 | 7 | 8 | 9 | 10 | 11 | 12 | 13 |
|---|---|---|---|---|---|---|---|---|---|---|---|---|---|---|
| Oxygen | Parts by | 0 | 0 | 1 | 0.02702 | 0.00004 | 0.00000 | 0.00003 | 0.00003 | 0.00000 | 0.00000 | 0.00003 | 0.00000 | 0.00033 |
| Hydrogen | mass | 0 | 0 | 0 | 0.00108 | 0.01328 | 0.00002 | 0.01416 | 0.01416 | 0.00043 | 0.00130 | 0.01505 | 0.00041 | 0.17381 |
| CO | | 0 | 0 | 0 | 0.00095 | 0.00611 | 0.00002 | 0.00650 | 0.00650 | 0.00043 | 0.00098 | 0.00689 | 0.00037 | 0.07307 |
| CO2 | | 0 | 0 | 0 | 0.02538 | 0.04160 | 0.00111 | 0.04436 | 0.04436 | 0.01757 | 0.02007 | 0.04610 | 0.01003 | 0.20971 |
| Methane | | 0 | 0 | 0 | 0.00109 | 0.00404 | 0.00003 | 0.00433 | 0.00433 | 0.00055 | 0.00098 | 0.00457 | 0.00042 | 0.04207 |
| Ethene | | 0 | 0 | 0 | 0.00936 | 0.01453 | 0.00041 | 0.01550 | 0.01550 | 0.00619 | 0.00723 | 0.01611 | 0.00372 | 0.06523 |
| Propane | | 1 | 0 | 0 | 0.81245 | 0.52809 | 0.00003 | 0.56349 | 0.56349 | 0.00044 | 0.65167 | 0.59076 | 0.19074 | 0.39869 |
| Propene | | 0 | 0 | 0 | 0.02563 | 0.28148 | 0.00006 | 0.30034 | 0.30034 | 0.00088 | 0.31475 | 0.31534 | 0.10706 | 0.02000 |
| Acetic acid | | 0 | 0 | 0 | 0.0000 | 0.00000 | 0.00000 | 0.00000 | 0.00000 | 0.00000 | 0.00000 | 0.00000 | 0.67522 | 0.01655 |
| Isopropyl acetate | | 0 | 0 | 0 | 0.00000 | 0.00000 | 0.00000 | 0.00000 | 0.00000 | 0.00000 | 0.00000 | 0.00000 | 0.00411 | 0.00034 |
| Isopropanol | | 0 | 0 | 0 | 0.00000 | 0.00000 | 0.00000 | 0.00000 | 0.00000 | 0.00000 | 0.00000 | 0.00000 | 0.00617 | 0.00020 |
| Benzene | | 0 | 0 | 0 | 0.00000 | 0.00000 | 0.00000 | 0.00000 | 0.00000 | 0.00000 | 0.00000 | 0.00000 | 0.00000 | 0.00000 |
| Water | | 0 | 1 | 0 | 0.09703 | 0.11081 | 0.99833 | 0.05130 | 0.05130 | 0.97351 | 0.00302 | 0.00515 | 0.00176 | 0.00000 |

| Stream | | 14 | 15 | 16 | 17 | 18 | 19 | 20 | 21 | 22 | 23 | 231 | 24 |
|---|---|---|---|---|---|---|---|---|---|---|---|---|---|
| Oxygen | Parts by | 0.00003 | 0.00000 | 0.00001 | 0.00000 | 0 | 0.00000 | 0.00000 | 0.00000 | 0.00000 | 0.00000 | 0.00000 | 0.00000 |
| Hydrogen | mass | 0.01199 | 0.00029 | 0.00202 | 0.00000 | 0 | 0.00000 | 0.00000 | 0.00000 | 0.00000 | 0.00000 | 0.00000 | 0.00000 |
| CO | | 0.00681 | 0.00030 | 0.00178 | 0.00000 | 0 | 0.00000 | 0.00000 | 0.00000 | 0.00000 | 0.00000 | 0.00000 | 0.00000 |
| CO2 | | 0.06148 | 0.00953 | 0.04743 | 0.00035 | 0 | 0.00016 | 0.00015 | 0.00015 | 0.00000 | 0.00023 | 0.02269 | 0.00000 |
| Methane | | 0.00514 | 0.00037 | 0.00203 | 0.00000 | 0 | 0.00000 | 0.00000 | 0.00000 | 0.00000 | 0.00000 | 0.00000 | 0.00000 |
| Ethene | | 0.02065 | 0.00356 | 0.01749 | 0.00016 | 0 | 0.00007 | 0.00007 | 0.00007 | 0.00000 | 0.00010 | 0.01029 | 0.00000 |
| Propane | | 0.75655 | 0.18707 | 0.88095 | 0.01400 | 0 | 0.00638 | 0.00584 | 0.00584 | 0.00000 | 0.00905 | 0.43513 | 0.00000 |
| Propene | | 0.03796 | 0.01052 | 0.04789 | 0.00116 | 0 | 0.00053 | 0.00048 | 0.00048 | 0.00000 | 0.00075 | 0.01872 | 0.00000 |
| Acetic acid | | 0.05232 | 0.53798 | 0.00000 | 0.67156 | 0 | 0.31310 | 0.28651 | 0.35872 | 0.98500 | 0.01000 | 0.00022 | 0.01122 |
| Isopropyl acetate | | 0.04579 | 0.24242 | 0.00000 | 0.30291 | 0 | 0.67446 | 0.61710 | 0.49429 | 0.00548 | 0.76650 | 0.40647 | 0.86177 |
| Isopropanol | | 0.00077 | 0.00619 | 0.00000 | 0.00773 | 0 | 0.00431 | 0.00408 | 0.07635 | 0.00952 | 0.11357 | 0.06405 | 0.12684 |
| Benzene | | 0.00000 | 0.00000 | 0.00000 | 0.00000 | 0 | 0.00003 | 0.00002 | 0.00002 | 0.00000 | 0.00004 | 0.00004 | 0.00007 |
| Water | | 0.00052 | 0.00178 | 0.00039 | 0.00212 | 1 | 0.00097 | 0.08575 | 0.06408 | 0.00000 | 0.09977 | 0.04240 | 0.00010 |

| Stream | | 25 | 251 | 26 | 27 | 28 | 29 | 30 | 31 | 311 | 32 | 33 | 34 |
|---|---|---|---|---|---|---|---|---|---|---|---|---|---|
| Oxygen | Parts by | 0.00000 | 0.00000 | 0.00000 | 0 | 0.00000 | 0.00000 | 0.00000 | 0.00000 | 0.00000 | 0.00000 | 0.00000 | 0 |
| Hydrogen | mass | 0.00000 | 0.00000 | 0.00000 | 0 | 0.00000 | 0.00000 | 0.00000 | 0.00000 | 0.00000 | 0.00000 | 0.00000 | 0 |
| CO | | 0.00000 | 0.00000 | 0.00000 | 0 | 0.00000 | 0.00000 | 0.00000 | 0.00000 | 0.00000 | 0.00000 | 0.00000 | 0 |
| CO2 | | 0.00000 | 0.01472 | 0.00000 | 0 | 0.00000 | 0.00000 | 0.00000 | 0.00000 | 0.02084 | 0.00000 | 0.00000 | 0 |
| Methane | | 0.00000 | 0.00000 | 0.00000 | 0 | 0.00000 | 0.00000 | 0.00000 | 0.00000 | 0.00000 | 0.00000 | 0.00000 | 0 |
| Ethene | | 0.00000 | 0.00667 | 0.00000 | 0 | 0.00000 | 0.00000 | 0.00000 | 0.00000 | 0.00945 | 0.00000 | 0.00000 | 0 |
| Propane | | 0.02190 | 0.59163 | 0.02375 | 0 | 0.02372 | 0.00013 | 0.00000 | 0.00037 | 0.05157 | 0.00000 | 0.00000 | 0 |
| Propene | | 0.00337 | 0.04582 | 0.00361 | 0 | 0.00360 | 0.01069 | 0.00000 | 0.03861 | 0.53684 | 0.00000 | 0.00000 | 0 |
| Acetic acid | | 0.00022 | 0.00000 | 0.00020 | 0 | 0.00020 | 0.00033 | 0.00044 | 0.00003 | 0.00000 | 0.01284 | 0.00000 | 1 |
| Isopropyl acetate | | 0.51157 | 0.14178 | 0.55487 | 0 | 0.55399 | 0.01852 | 0.00000 | 0.06900 | 0.10835 | 0.98567 | 0.00197 | 0 |
| Isopropanol | | 0.16473 | 0.05437 | 0.17847 | 0 | 0.17818 | 0.17397 | 0.00224 | 0.64405 | 0.18781 | 0.00144 | 0.99700 | 0 |
| Benzene | | 0.20091 | 0.11999 | 0.21792 | 1 | 0.21915 | 0.00192 | 0.00000 | 0.00707 | 0.04258 | 0.0005 | 0.00023 | 0 |
| Water | | 0.09729 | 0.02500 | 0.02118 | 0 | 0.02115 | 0.79444 | 0.99732 | 0.24087 | 0.04257 | 0.00000 | 0.00079 | 0 |

C) compressing said product gas stream (b) and optionally separating said product gas stream (b) into an aqueous phase (c1), a phase (c2) comprising said alkene (III) and said alkane (II), and optionally comprising high boilers, and a gas phase (c3) comprising hydrogen and low boilers;

D) reacting said product gas stream (b) or said phase (c2) with an organic acid (IV) in an esterification zone to obtain a product mixture (d) comprising the corresponding alkyl ester (V) of said organic acid (IV) and said unconverted alkane (II);

E) removing from said product mixture (d) a gas stream (e1), which comprises said alkane (II) and is optionally recycled into said dehydrogenation zone, and a product mixture (e2) comprising said alkyl ester (V);

F) reacting said product mixture (e2) with water in an ester hydrolysis zone to give a product mixture (f) comprising said alkanol (I) and said organic acid (IV);

G) removing said alkanol (I) and said organic acid (IV) from said product mixture (f) and optionally recycling said organic acid (IV) into said esterification zone;

wherein said alkanol (I) is selected from the group consisting of isopropanol and 2-butanol;

wherein when said alkanol (I) is isopropanol, its corresponding alkane (II) is propane and when said alkanol (I) is 2-butanol, its corresponding alkane (II) is n-butane; and wherein when said alkane (II) is propane, its corresponding alkene (III) is propene and when said alkane is n-butane, its corresponding alkene (III) are butenes.

2. The process of claim 1, wherein said dehydrogenation is performed in the presence of oxygen.

3. The process of claim 1, wherein said dehydrogenation is performed in the presence of steam.

4. The process of claim 1, wherein step F) is performed in a reactive distillation column.

5. The process of claim 1, wherein step F) is at least partly performed in an ester hydrolysis prereactor and at least partly performed in a reactive distillation column.

6. The process of claim 1, wherein said water in step F) is used in a stoichiometric deficiency.

7. The process according to claim 1, wherein
said organic acid (IV) is formic acid
said product mixture (e2) comprises isopropyl formate,
said product mixture (e2) is reacted with water in an ester hydrolysis reactor to give a product mixture (f) comprising isopropanol, formic acid, isopropyl formate, and water,
said product mixture (f) is separated in a first distillation column into a stream (g1) comprising formic acid and water, and a stream (g2) comprising isopropyl formate, isopropanol, and water, wherein stream (g1) is recycled into said esterification zone
said stream (g2) is separated in a second distillation column into a stream (g4) comp rising isopropyl formate, water, and isopropanol, and a stream (g3) consisting essentially of isopropanol, wherein stream (g4) is recycled into said ester hydrolysis reactor.

8. The process of claim 7, wherein water is additionally removed from formic acid in stream (g1) and concentrated formic acid is recycled into the esterification zone.

9. The process of claim 1, wherein
said organic acid (IV) is formic acid,
said product mixture (e2) is reacted with water in an ester hydrolysis reactor to give a product mixture (f) comprising isopropanol, formic acid, isopropyl formate, and water,
said product gas mixture (f) is conducted into a dividing wall distillation column on one side of the dividing wall and separated into a stream (g1) comprising formic acid and water, a distillate stream (g4) comprising isopropyl formate, water, and isopropanol, and a side stream (g3) on the far side of the dividing wall consisting essentially of isopropanol, wherein stream (g1) is recycled into said esterification zone and stream (g4) into said ester hydrolysis reactor.

10. The process of claim 1, wherein
said product mixture (e2) is reacted with water in a preliminary ester hydrolysis reactor to give a product mixture (f) comprising said alkanol (I), said organic acid (IV), said alkyl ester (V) and water,
a product mixture (f2) comprising said alkanol (I), said alkyl ester (V), and water, and a stream (f3) comprising said organic acid (IV) are obtained from said product mixture (f) in a reactive distillation column, wherein said stream (f3) is recycled into said esterification zone, and
said product mixture (f2) is separated in a downstream distillation column into a stream (g1) consisting essentially of said alkanol (I), said alkyl ester (V), and water, and a stream (g2) comprising said alkanol (I), wherein said stream (g1) is recycled into said ester hydrolysis zone.

11. The process of claim 10, wherein
said organic acid (IV) is acetic acid,
said product mixture (f) comprises isopropanol, acetic acid, isopropyl acetate and water,
said product mixture (f2) consists essentially of isopropanol, isopropyl acetate, and water,
said stream (f3) consists essentially of acetic acid,
said stream (g1) consists essentially of isopropanol, isopropyl acetate, and water, and
said stream (g2) consists essentially of isopropanol.

12. The process of claim 1, wherein
said organic acid (IV) is acetic acid,
said product mixture (e2) is fed with water directly into a reactive distillation column,
a product mixture (f2) consisting essentially of isopropanol, isopropyl acetate and water, and a stream (f3) consisting essentially of acetic acid, are obtained from said product mixture (e2) in said reactive distillation column, wherein said stream (f3) is recycled into said esterification zone, and
said product mixture (f2) is separated in a distillation column into a stream (g1) consisting essentially of isopropanol, isopropyl acetate, and water, and a stream (g2) consisting essentially of isopropanol, wherein stream (g1) is recycled into said reactive distillation column.

13. The process of claim 1, wherein
said organic acid (IV) is acetic acid,
said product mixture (e2) is fed with water directly into a reactive distillation column,
a product mixture (f2) consisting essentially of isopropanol, water, and isopropyl acetate, and a stream (f3) consisting essentially of acetic acid and a homogeneous catalyst, are obtained from said product mixture (e2) in said reactive distillation column and recycled wherein said stream (f3) is recycled into said esterification zone, and
said product mixture (f2) is separated in a distillation column into a stream (g1) consisting essentially of isopropyl acetate, water, and isopropanol, and a stream (g2) consisting essentially of isopropanol, wherein stream (g1) is recycled into said reactive distillation column.

14. The process of claim 1, wherein, said product mixture (e2) is reacted with water in an ester hydrolysis reactor to give a product mixture (f) comprising isopropanol, formic acid, isopropyl formate, and water, a product mixture (f2) consisting essentially of isopropanol and isopropyl formate, and a stream (f3) consisting essentially of formic acid and water, are obtained from said product mixture (f) in a reactive distillation column, wherein said stream (f3) is recycled into said esterification zone, and said product mixture (f2) is separated in a distillation column into a stream (g1) consisting essentially of isopropanol and isopropyl formate and a stream (g2) consisting essentially of isopropanol, wherein said stream (g1) is recycled into said reactive distillation column.

15. A process for preparing isopropanol from propane, comprising:

A) providing a starting gas stream (a) comprising propane;

B) feeding said starting gas stream (a) into a dehydrogenation zone and dehydrogenating said propane to propene to obtain a product gas stream (b) comprising propene, unconverted propane, steam, hydrogen, and low boilers, and optionally comprising high boilers;

C) compressing said product gas stream (b) and optionally separating said product gas stream (b) into an aqueous phase (c1), a phase (c2) comprising propene and propane, and optionally comprising high boilers, and a gas phase (c3) comprising hydrogen and low boilers;

D) reacting said product gas stream (b) or said phase (c2) with acetic acid in an esterification zone to obtain a product mixture (d) comprising isopropyl acetate and said unconverted propane;

E) removing from said product mixture (d) a gas stream (e1), which comprises propane and is optionally recycled into said dehydrogenation zone, and a product mixture (e2) comprising isopropyl acetate;

F) reacting said product mixture (e2) with water in an ester hydrolysis zone to give a product mixture (f) comprising isopropanol, acetic acid, isopropyl acetate, and water;

G) separating said product mixture (f) in a first distillation column into a stream (g1) consisting essentially of acetic acid and a stream (g2) comprising isopropyl acetate, isopropanol, and water, and recycling said stream (g1) into said esterification zone;

H) separating said stream (g2) in a second distillation column into a stream (h1) comprising isopropyl acetate and isopropanol, and a stream (h2) consisting essentially of isopropanol and water.

16. The process of claim 15, wherein said dehydrogenation is performed in the presence of oxygen.

17. The process of claim 15, wherein said dehydrogenation is performed in the presence of steam.

18. The process of claim 15, wherein F) is performed in a reactive distillation column.

19. The process of claim 15, wherein F) is at least partly performed in an ester hydrolysis prereactor and at least partly performed in a reactive distillation column.

20. The process of claim 15, wherein said water in F) is used in a stoichiometric deficiency.

21. The process of claim 20, further comprising

I) removing isopropanol as a distillate from said stream (h1) in a further column to obtain a stream (i1) which consists essentially of isopropyl acetate and is recycled into said ester hydrolysis reactor.

\* \* \* \* \*